(12) United States Patent
Greenhalgh et al.

(10) Patent No.: US 9,968,373 B1
(45) Date of Patent: May 15, 2018

(54) HANDLES FOR NEEDLE ASSEMBLIES

(71) Applicant: SURGICAL DEVICE EXCHANGE, LLC, Boca Raton, FL (US)

(72) Inventors: Travis Greenhalgh, Boca Raton, FL (US); Ryan Lewis, Waxhaw, NC (US)

(73) Assignee: SurGenTec, LLC, Boca Raton, FL (US)

( * ) Notice: Subject to any disclaimer, the term of this patent is extended or adjusted under 35 U.S.C. 154(b) by 0 days. days.

(21) Appl. No.: 14/734,925

(22) Filed: Jun. 9, 2015

Related U.S. Application Data

(63) Continuation-in-part of application No. 14/626,765, filed on Feb. 19, 2015, now abandoned.

(60) Provisional application No. 61/943,240, filed on Feb. 21, 2014.

(51) Int. Cl.
*A61B 10/00* (2006.01)
*A61B 17/34* (2006.01)
*A61B 17/00* (2006.01)

(52) U.S. Cl.
CPC ...... *A61B 17/3403* (2013.01); *A61B 17/3421* (2013.01); *A61B 17/3478* (2013.01); *A61B 17/3472* (2013.01); *A61B 2017/0046* (2013.01); *A61B 2017/00469* (2013.01); *A61B 2017/3405* (2013.01)

(58) Field of Classification Search
CPC ..................................................... A61B 5/00
USPC ......... 600/562, 564, 566, 567; 606/86 R, 96, 606/97, 67
See application file for complete search history.

(56) References Cited

U.S. PATENT DOCUMENTS

| | | | | |
|---|---|---|---|---|
| 4,443,941 A | * | 4/1984 | McPhaul | A61B 17/8863 30/182 |
| 4,793,363 A | * | 12/1988 | Ausherman | A61B 10/025 600/567 |
| 4,917,111 A | * | 4/1990 | Pennig | A61B 17/1703 606/97 |
| 5,250,054 A | | 10/1993 | Li | |
| 5,368,046 A | | 11/1994 | Scarfone | |
| 5,403,321 A | * | 4/1995 | DiMarco | A61B 17/1721 606/96 |
| 5,480,389 A | | 1/1996 | McWha et al. | |
| 5,649,946 A | * | 7/1997 | Bramlet | A61B 17/320036 606/159 |
| 5,665,086 A | * | 9/1997 | Itoman | A61B 17/921 606/62 |
| 5,693,031 A | * | 12/1997 | Ryan | A61B 17/3496 604/167.03 |

(Continued)

*Primary Examiner* — May Abouelela
(74) *Attorney, Agent, or Firm* — Knobbe, Martens, Olson & Bear, LLP

(57) ABSTRACT

An impact or extension handle for a needle assembly such as a jamshidi needle can include an attachment portion and a handle portion. The impact or extension handle can also include an impact strikeplate. The attachment portion is configured to couple to the jamshidi needle. A user can use the impact or extension handle to manipulate the position or angle of the needle assembly. A user can tap a mallet or similar instrument on the impact strikeplate to drive the needle assembly into a target location in a patient's body. The impact or extension handle can allow the user to hold his or her hands out of the way of equipment used during the procedure and away from potentially harmful radiation from imaging equipment used during the procedure.

30 Claims, 36 Drawing Sheets

(56) References Cited

U.S. PATENT DOCUMENTS

| | | | | |
|---|---|---|---|---|
| 5,755,721 A * | 5/1998 | Hearn | | A61B 17/1728 606/104 |
| 5,807,275 A * | 9/1998 | Jamshidi | | A61B 10/025 600/567 |
| 6,019,776 A | 2/2000 | Preissman et al. | | |
| 6,066,146 A | 5/2000 | Carroll et al. | | |
| 6,083,176 A * | 7/2000 | Terwilliger | | A61B 10/0233 600/562 |
| 6,197,002 B1 | 3/2001 | Peterson | | |
| 6,241,734 B1 * | 6/2001 | Scribner | | A61B 17/8816 606/93 |
| 6,283,925 B1 * | 9/2001 | Terwilliger | | A61B 10/0233 600/562 |
| 6,371,959 B1 * | 4/2002 | Trice | | A61B 17/1725 606/97 |
| 6,656,189 B1 | 12/2003 | Wilson et al. | | |
| 7,033,365 B2 * | 4/2006 | Powell | | A61B 17/921 606/104 |
| 7,278,972 B2 * | 10/2007 | Lamoureux | | A61B 10/025 600/562 |
| 7,643,884 B2 | 1/2010 | Pond, Jr. et al. | | |
| 7,657,308 B2 | 2/2010 | Miles et al. | | |
| 7,942,826 B1 | 5/2011 | Scholl et al. | | |
| 7,963,927 B2 | 6/2011 | Kelleher et al. | | |
| 9,976,498 | 7/2011 | Swisher et al. | | |
| 8,062,259 B2 | 11/2011 | Nycz et al. | | |
| 8,162,889 B2 | 4/2012 | Swisher et al. | | |
| 8,162,967 B1 * | 4/2012 | Kaiser | | A61B 17/1604 279/82 |
| 8,192,443 B2 | 6/2012 | Perez-Cruet | | |
| 8,255,044 B2 | 8/2012 | Miles et al. | | |
| 8,784,330 B1 | 7/2014 | Scholl et al. | | |
| 8,992,442 B2 * | 3/2015 | Cortes Ramirez | | A61B 10/025 600/562 |
| 9,101,432 B2 * | 8/2015 | Limouze | | A61B 17/1725 |
| 9,155,574 B2 * | 10/2015 | Saravia | | A61B 17/7208 |
| 9,192,398 B2 * | 11/2015 | Siravo | | A61B 17/1703 |
| 2002/0032447 A1 * | 3/2002 | Weikel | | A61B 17/1671 606/86 R |
| 2002/0042581 A1 * | 4/2002 | Cervi | | A61B 10/025 600/567 |
| 2002/0099385 A1 * | 7/2002 | Ralph | | A61B 17/1686 606/92 |
| 2004/0068264 A1 * | 4/2004 | Treace | | A61B 17/1635 606/86 R |
| 2005/0038444 A1 * | 2/2005 | Binder, Jr. | | A61B 17/1728 606/96 |
| 2005/0113838 A1 * | 5/2005 | Phillips | | A61B 17/1604 606/80 |
| 2005/0119663 A1 * | 6/2005 | Keyer | | A61B 17/1622 606/96 |
| 2007/0066987 A1 * | 3/2007 | Scanlan, Jr. | | A61B 10/025 606/184 |
| 2007/0260255 A1 | 11/2007 | Haddock | | |
| 2008/0200915 A1 | 8/2008 | Globerman | | |
| 2008/0234678 A1 * | 9/2008 | Gutierrez | | A61B 17/7086 606/60 |
| 2009/0024056 A1 | 1/2009 | Bacon et al. | | |
| 2009/0216260 A1 * | 8/2009 | Souza | | A61B 17/3417 606/185 |
| 2009/0254094 A1 * | 10/2009 | Knapp | | A61B 17/1637 606/96 |
| 2010/0069843 A1 * | 3/2010 | Allee | | A61B 10/025 604/117 |
| 2010/0121338 A1 * | 5/2010 | Pandya | | A61B 17/1684 606/96 |
| 2010/0191296 A1 * | 7/2010 | Lyon | | A61B 17/3417 606/86 R |
| 2010/0324556 A1 * | 12/2010 | Tyber | | A61B 17/1717 606/62 |
| 2011/0093024 A1 | 4/2011 | Layne et al. | | |
| 2011/0276064 A1 * | 11/2011 | Henrichsen | | A61B 17/0469 606/145 |
| 2012/0059380 A1 * | 3/2012 | Deangelo | | A61B 17/8819 606/94 |
| 2012/0197320 A1 * | 8/2012 | Bereczki | | A61B 17/1671 606/86 R |
| 2012/0226301 A1 | 9/2012 | Geist | | |
| 2012/0239050 A1 | 9/2012 | Linderman et al. | | |
| 2012/0253353 A1 | 10/2012 | McBride | | |
| 2013/0345765 A1 * | 12/2013 | Brockman | | A61B 17/8855 606/86 R |
| 2015/0112354 A1 * | 4/2015 | Bourque | | A61F 2/4601 606/99 |

* cited by examiner

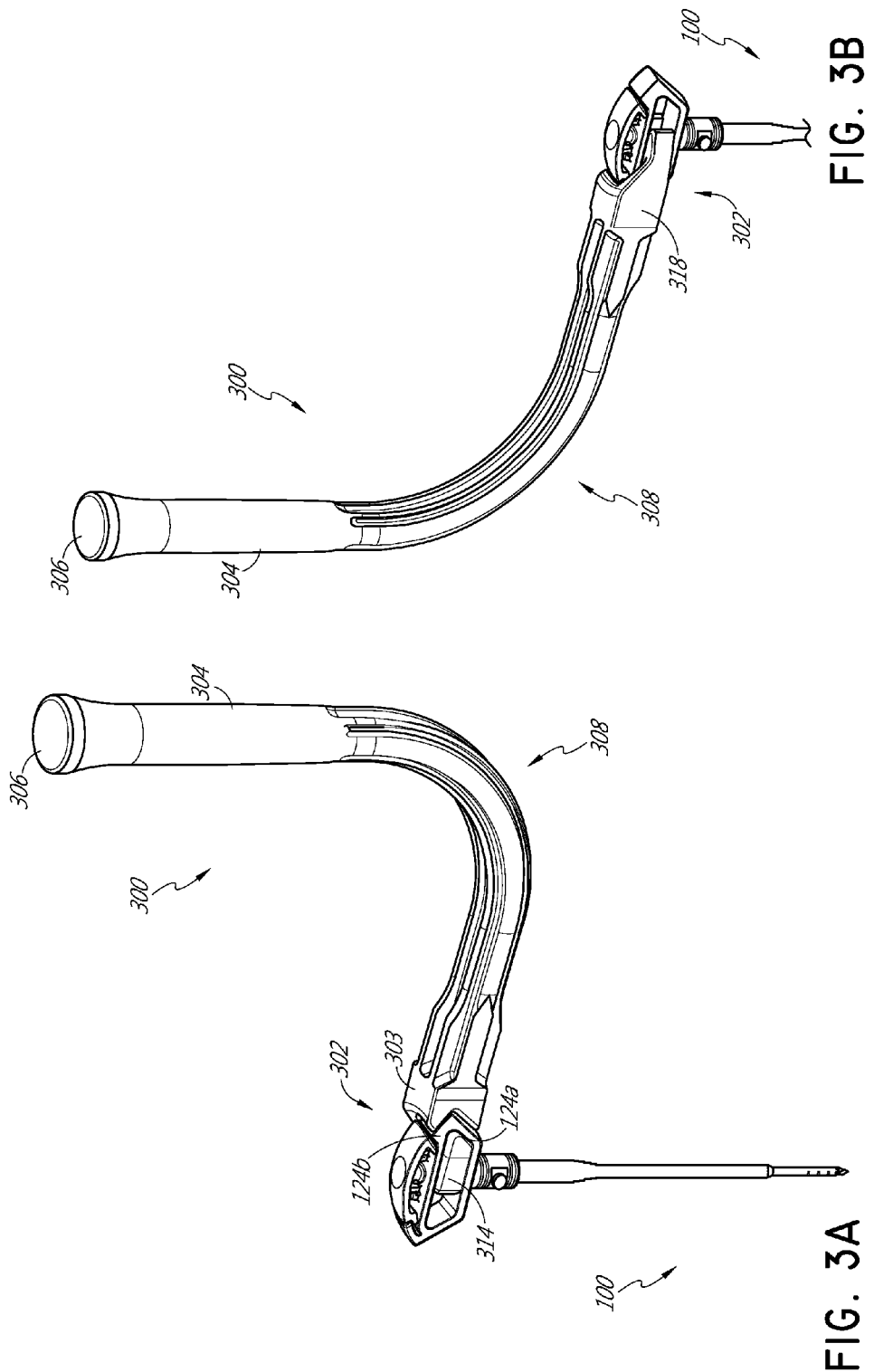

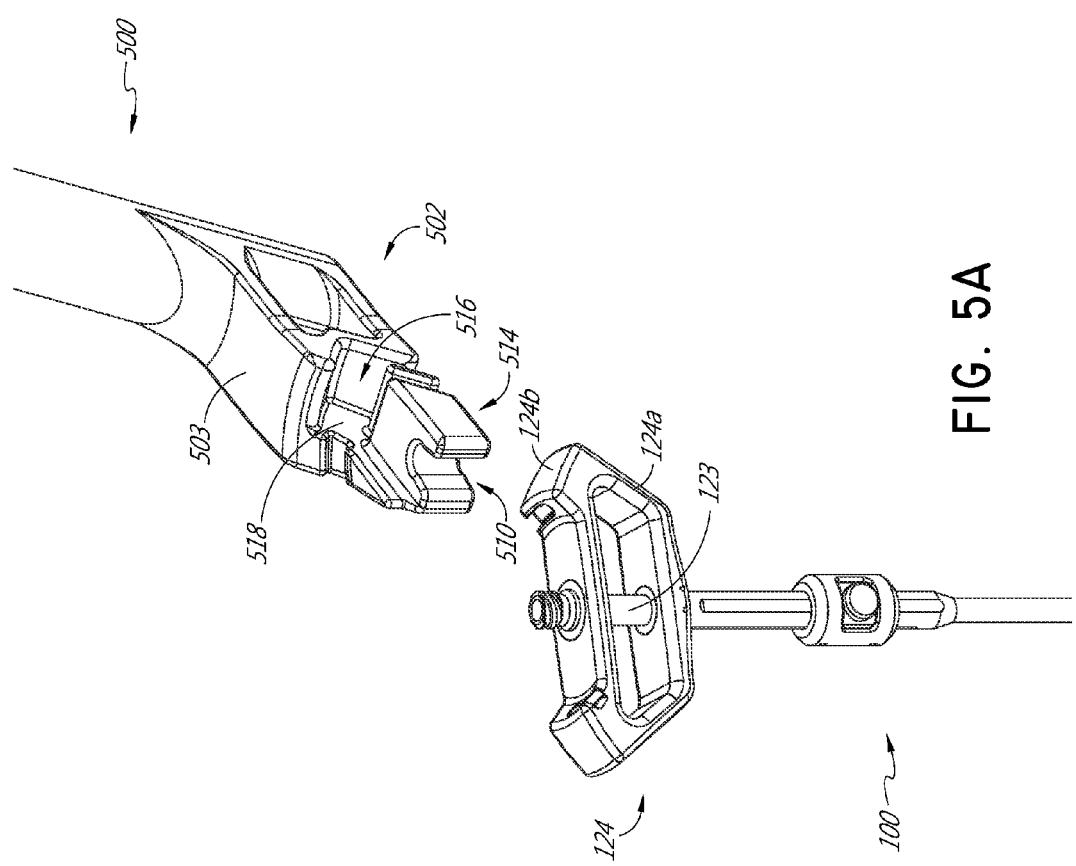

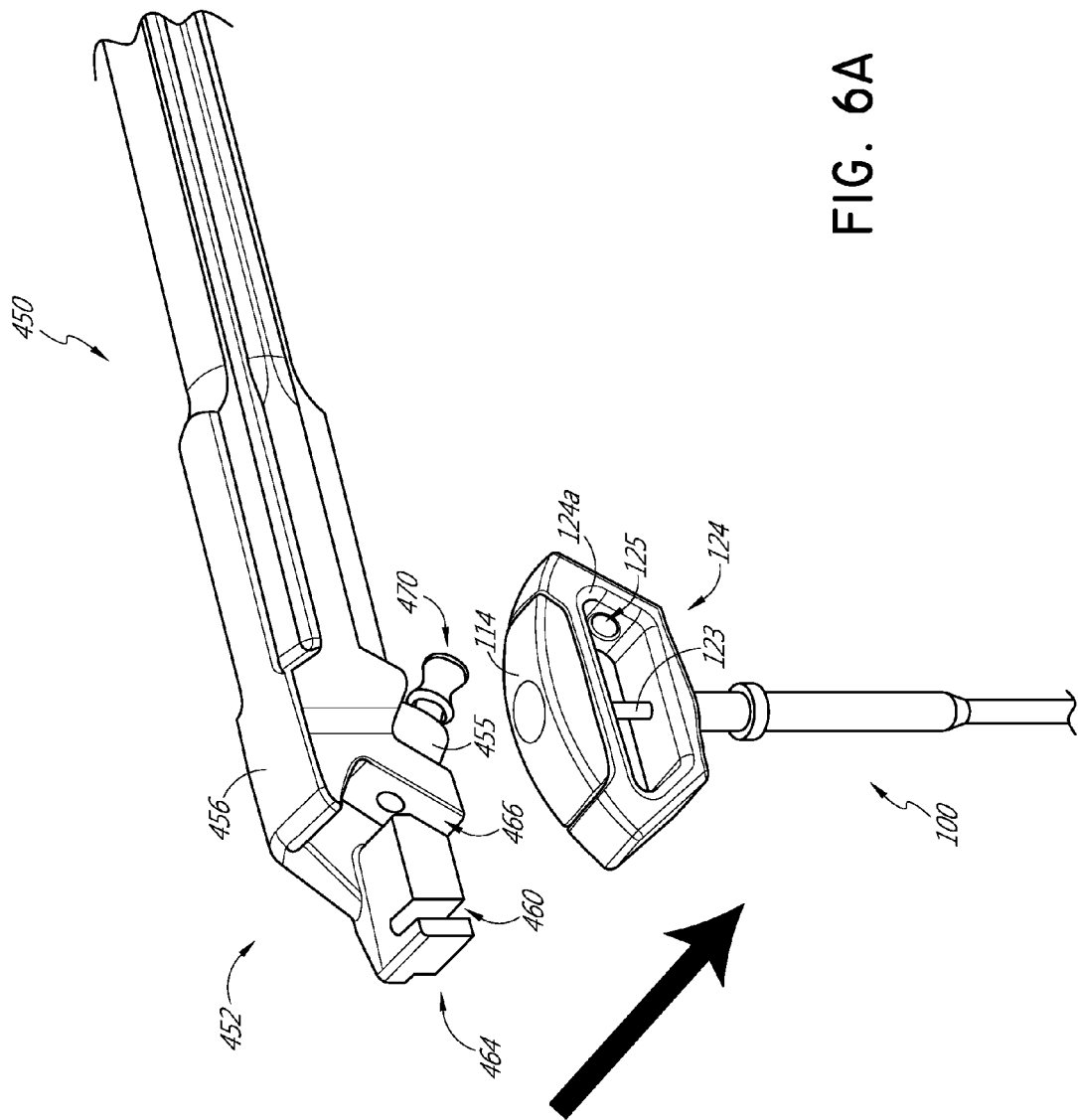

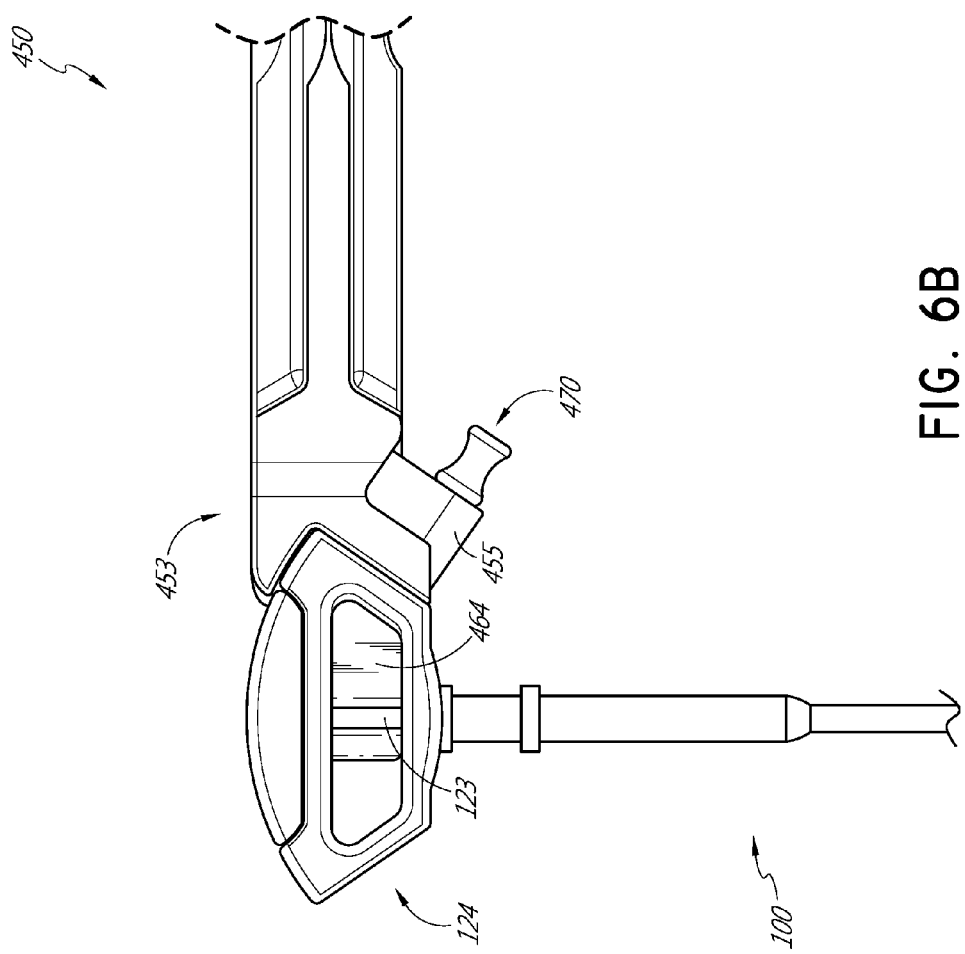

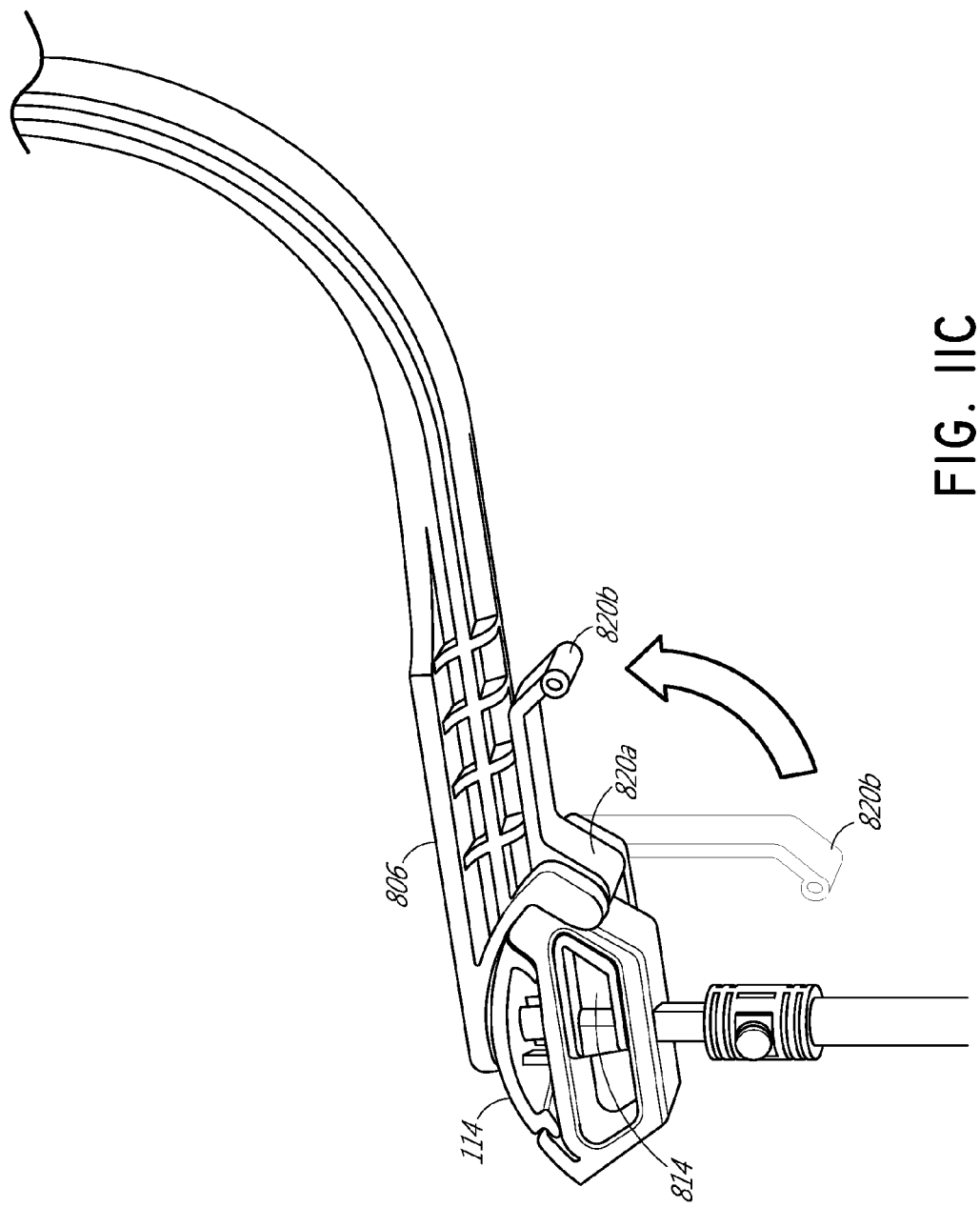

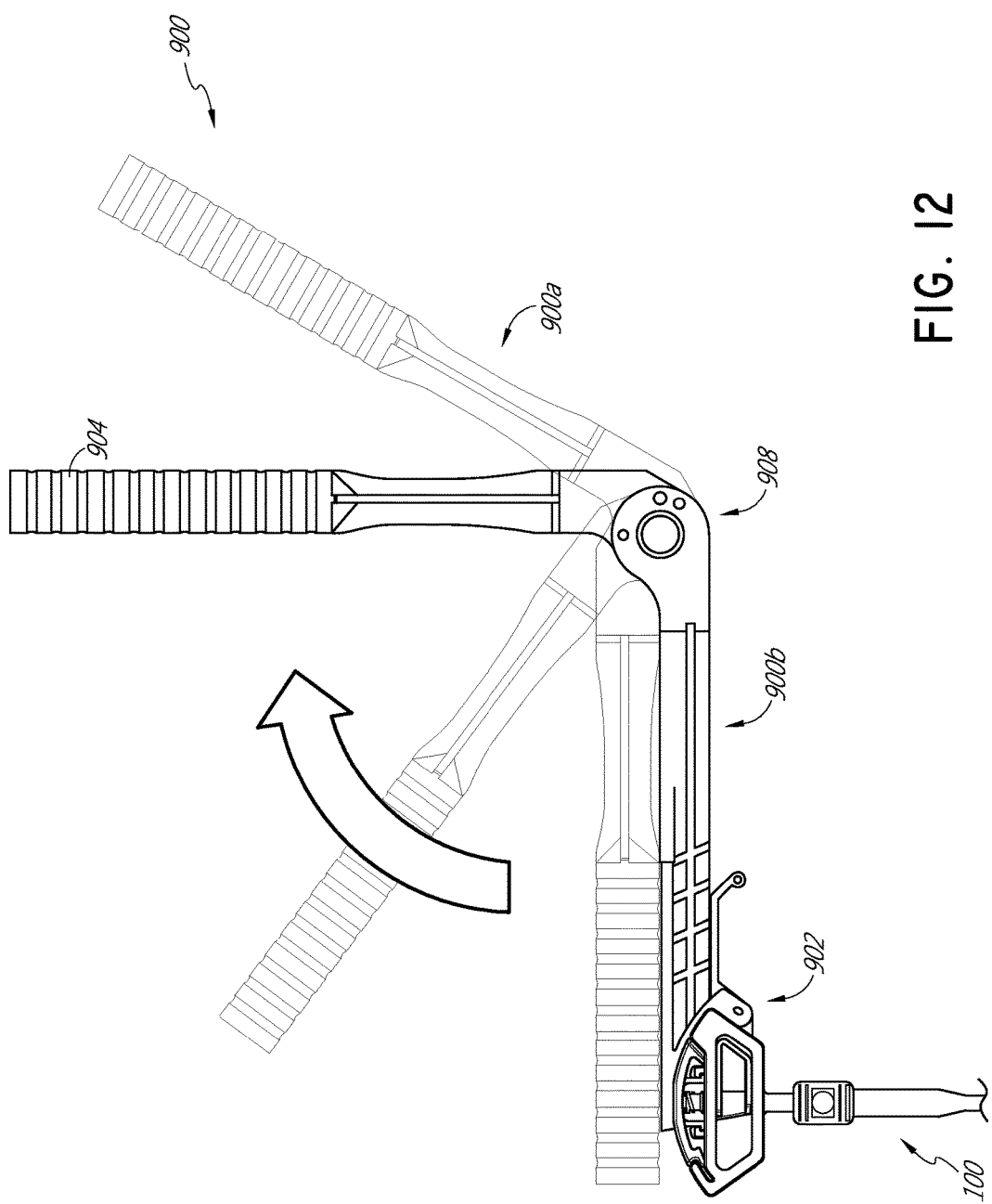

HANDLES FOR NEEDLE ASSEMBLIES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation-in-part of U.S. application Ser. No. 14/626,765, filed Feb. 19, 2015, which claims priority benefit of U.S. Provisional Application No. 61/943,240, filed Feb. 21, 2014, the entirety of each of which is hereby incorporated by reference.

BACKGROUND

Field

The present application relates to orthopedic surgery in general, and more particularly, to handles for use with needle assemblies.

Description of the Related Art

Jamshidi type needles are used for a variety of procedures, for example, for bone marrow biopsies, delivering bone graft and/or other materials to a target location, or to access a target location and form a pilot hole, for example to access a pedicle for delivery of a pedicle screw. In some cases the user, such as a surgeon or other medical professional, may have difficulty finding and/or manipulating the needle to the correct or desired angle and/or position to advance the target needle to the target location. In some procedures, the user may use various intraoperative imaging modalities, for example, a C-arm, to help guide the jamshidi and/or other instruments or devices to the desired location. In some procedures, the user may use a mallet or similar instrument to drive the jamshidi needle into a target location, such as a target bone. However, if the user must hold the jamshidi and/or use a mallet on the jamshidi itself, the user's hands may be in the way of imaging equipment and/or may be exposed to ionizing radiation from the imaging equipment.

SUMMARY

Various embodiments of handles configured to be used with needle assemblies are described herein. A user can use a handle according to the present disclosure to maneuver a needle assembly to a desired position, angle, or orientation to allow the user to access a target location in a patient's body with the needle assembly. In some embodiments, the user can use a handle as described herein to mallet or otherwise drive a needle assembly into a target location, such as a target bone.

In some embodiments an impact handle for use with a needle assembly includes an attachment portion, a handle portion, and an impact strikeplate. The attachment portion is configured to couple to the needle assembly. The handle portion extends from the attachment portion and is configured to be gripped by a user, such as a surgeon or other medical personnel, a surgical robot, or other stabilization method or device, in use. The impact strikeplate is configured to be struck with a mallet or similar instrument in use and configured to transfer forces from the mallet or similar instrument to the needle assembly. In some embodiments, a kit includes a needle assembly and an impact handle.

In some embodiments, the handle portion of the impact handle extends from the attachment portion at an angle. In some embodiments, the impact strikeplate is on a proximal end of the handle portion. In other embodiments, a top surface of the attachment portion includes the impact strikeplate. In some embodiments, both a proximal end of the handle portion and a top surface of the attachment portion can include impact strikeplates. In some embodiments, the top surface of the attachment portion extends over at least a part of a handle portion of the needle assembly when the attachment portion is coupled to the needle assembly. In some embodiments, the attachment portion extends generally horizontally when coupled to the needle assembly, the handle portion extends generally vertically when the attachment portion is coupled to the needle assembly, and a curved portion extends between the attachment portion and handle portion. In some embodiments, the attachment portion includes a locking mechanism configured to secure the attachment portion to the needle assembly in a locked position.

The needle assembly can include a cannula shaft and a cannula handle coupled to a proximal end of the cannula shaft, and the attachment portion can be configured to couple to a portion of the cannula shaft. In some embodiments, the cannula handle has a central opening and a portion of the cannula shaft extends across the central opening. The attachment portion of the impact handle can include a connector configured to be disposed in the central opening when the attachment portion is coupled to the needle assembly. The connector can include a notch configured to engage the portion of the cannula shaft extending across the central opening. In some such embodiments, the attachment portion includes a recess configured to receive a side of the cannula handle when the attachment portion is coupled to the needle assembly, and the recess is partially bordered by the connector. In some embodiments, the side of the cannula handle includes a slot, and the attachment portion includes a locking cam configured to secure the impact handle to the needle assembly in a locked position. The locking cam can include a tab configured to be received in the slot when the attachment portion is coupled to the needle assembly and the locking cam is in the locked position.

In some embodiments, a method of driving a needle assembly, such as a jamshidi needle, into a target location in a patient's body includes coupling an impact handle to the jamshidi needle. The needle assembly includes a cannula shaft coupled to a cannula handle. The impact handle includes an attachment portion, a handle portion, and an impact strikeplate. Coupling the impact handle to the needle assembly can include engaging the attachment portion with a portion of the cannula shaft and a portion of the cannula handle. The method further includes tapping the impact strikeplate with a mallet or similar instrument to drive the needle assembly into the target location.

In some such embodiments, the needle assembly includes a cannula shaft coupled to a cannula handle, and coupling the impact handle to the portion of the needle assembly includes engaging the attachment portion with a portion of the cannula shaft and a portion of the cannula handle. In some such embodiments, the attachment portion of the impact handle includes a locking cam, and coupling the impact handle to the needle assembly further includes moving the locking cam to a locked position to secure the impact handle to the needle assembly. In some embodiments, the needle assembly includes a cannula shaft, and coupling the impact handle to the portion of the needle assembly includes engaging the attachment portion with a portion of the cannula shaft.

In some embodiments, a kit includes a needle assembly and an extension handle configured to be coupled to the needle assembly. The needle assembly includes a stylet having a sharp distal tip and a cannula. The cannula includes a cannula shaft and a cannula handle coupled to a proximal end of the cannula shaft. The cannula shaft has a lumen therethrough, and the stylet is configured to be disposed in the lumen of the cannula shaft. The extension handle includes an attachment portion configured to couple to the needle assembly and a handle portion extending from the attachment portion and configured to be gripped in use.

In some embodiments, the attachment portion of the extension handle is configured to couple to a portion of the cannula shaft. In some such embodiments, the cannula handle includes a central opening and a portion of the cannula shaft extends across the central opening. The attachment portion of the extension handle includes a connector configured to be disposed in the central opening when the attachment portion is coupled to the needle assembly. The connector can include a notch configured to engage the portion of the cannula shaft extending across the central opening.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 3A illustrates a front perspective view of another example embodiment of an impact handle coupled to the Jamshidi needle;

FIG. 3B illustrates a partial rear perspective view of the impact handle coupled to the Jamshidi needle of FIG. 3A;

FIG. 5A illustrates a partial front perspective of another example embodiment of an impact handle before being coupled to the Jamshidi needle;

FIG. 6A illustrates a partial front perspective view of another example embodiment of an impact handle before being coupled to a Jamshidi needle;

FIG. 6B illustrates a front view of the impact handle coupled to the Jamshidi needle of FIG. 6A;

FIG. 11C illustrates a partial front perspective view of the impact handle of FIGS. 11A-11B coupled to the Jamshidi needle showing two possible positions of a locking cam;

FIG. 11I illustrates a partial front section view of the impact handle of FIGS. 11F-11H coupled to the Jamshidi needle in the locked position;

FIG. 12 illustrates a front view of an example embodiment of a folding impact handle coupled to the Jamshidi needle;

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1A:
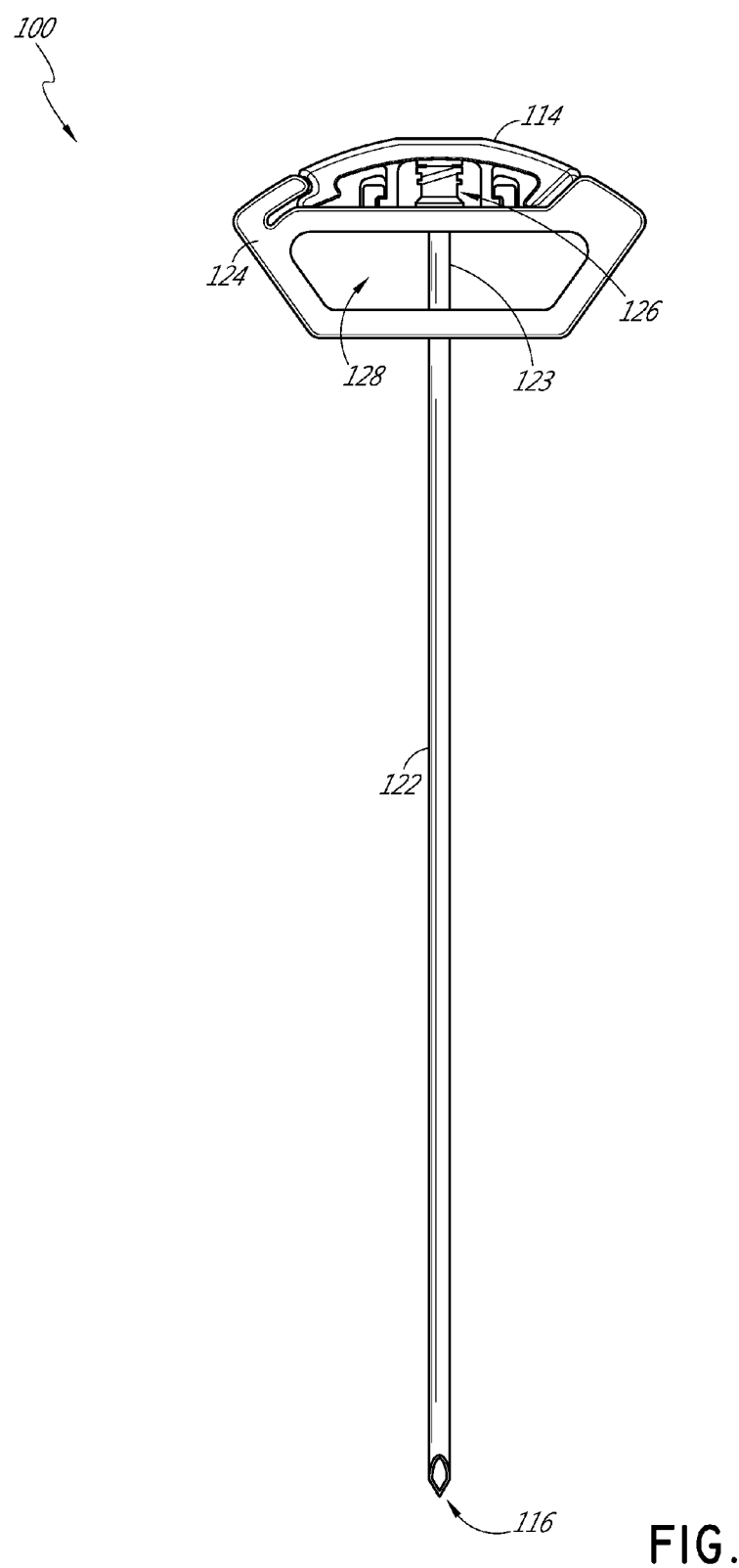
FIGS. 1A-1C illustrate an example embodiment of a Jamshidi needle.
Figure 1B:
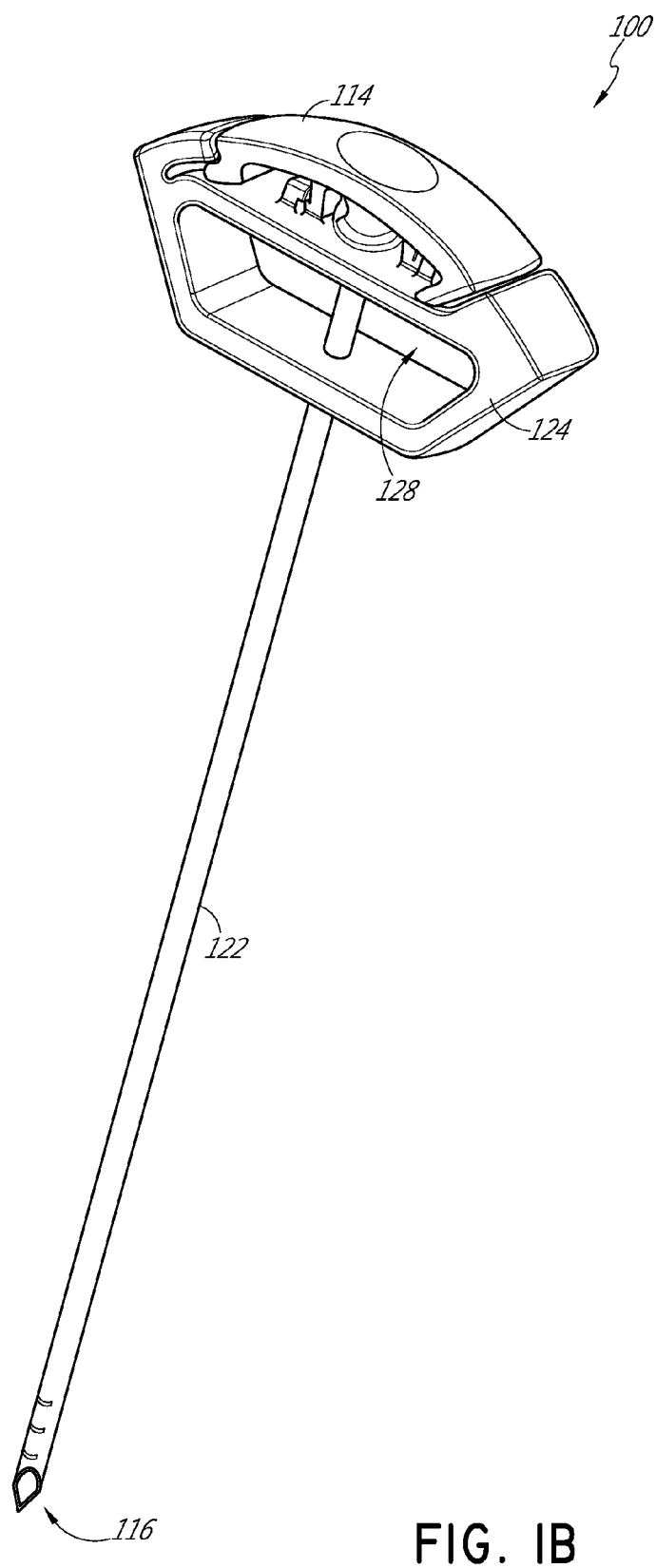
Figure 1C:
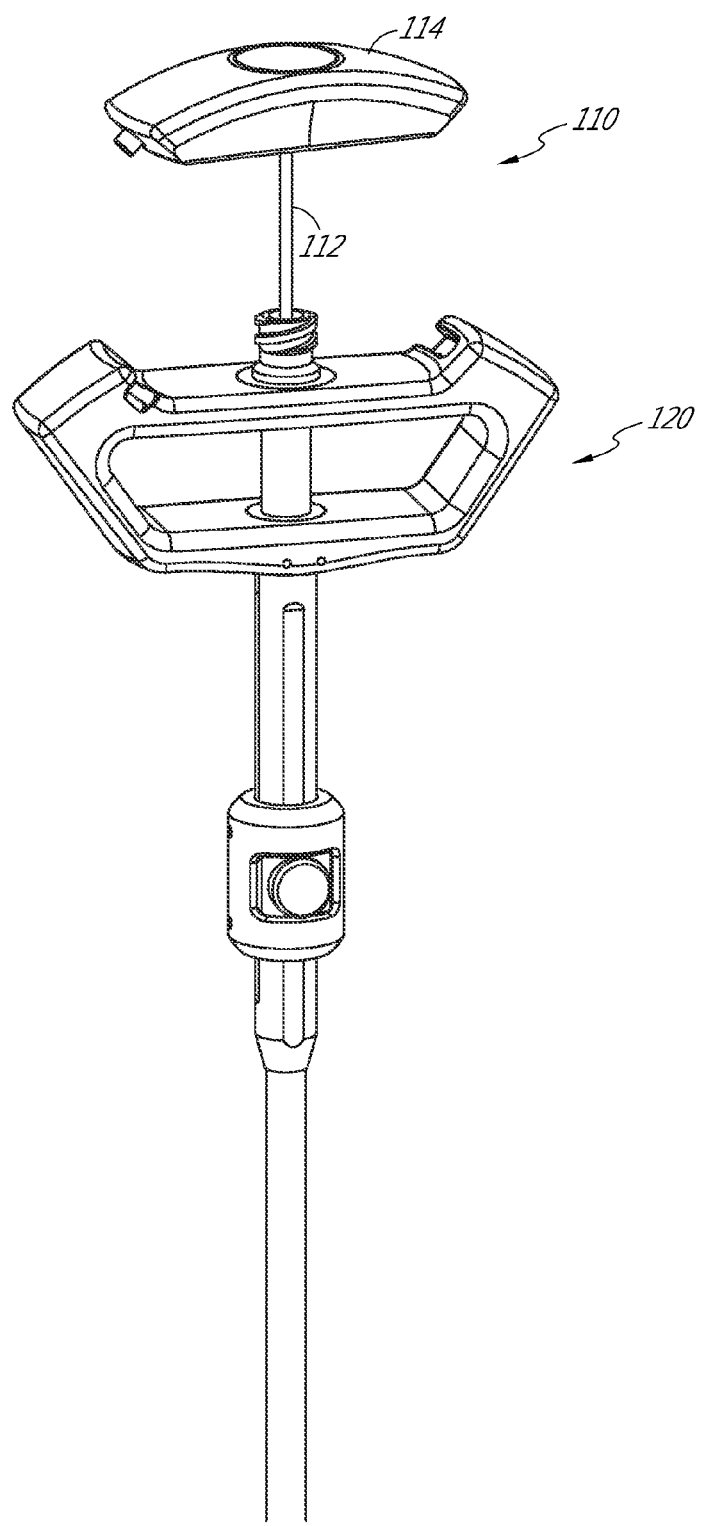

FIGS. 1A-1C illustrate an example embodiment of a needle assembly 100. The needle assembly 100 can be a Jamshidi-type needle as shown. The needle assembly 100 can be used for various procedures, for example, to perform bone marrow biopsies, deliver bone graft or other material(s) to a desired location, or access a target location and form a pilot hole, for example to access a pedicle for delivery of a pedicle screw. However, these are only sample procedures, and the needle assemblies and impact handles described herein can be used in a variety of procedures. The needle assembly 100 generally includes a stylet 110 and a cannula 120, as shown in FIG. 1C. The stylet 110 includes a stylet shaft 112 and a stylet handle 114 coupled to a proximal end of the stylet shaft 112. The cannula 120 includes a cannula shaft 122 having a lumen therethrough and a cannula handle 124 coupled to a proximal end of the cannula shaft 122. In the illustrated embodiment, the cannula handle 124 includes a central opening 128. As shown, a portion of the cannula shaft 122, post 123, extends across the central opening 128 to a proximal portion of the cannula handle 124. The lumen of the cannula 120 is configured to removably receive the stylet 110. A distal end of the stylet shaft 112 includes a penetrating tip 116 configured to extend beyond a distal end of the cannula shaft 122 when the stylet 110 is inserted into the cannula 120. In some embodiments, the stylet handle 114 and cannula handle 124 include features configured to lockingly engage each other to selectively lock the stylet 110 to the cannula 120.

In use, the needle assembly 100 is advanced to a target location using the penetrating tip 116 of the stylet 110 to penetrate tissue. In some procedures, the user, such as a surgeon or other medical professional, may use various intraoperative imaging modalities to help guide the needle assembly 100 and/or other instruments or devices to the desired location. For example, in some embodiments, the user may use a C-arm to guide introduction and placement of the needle assembly 100. Once the needle assembly 100 is in place, the stylet handle 114 can be unlocked from the cannula handle 124, and the stylet 110 can be removed from the cannula 120. In some embodiments, the cannula handle 124 includes a coupling 126, for example, a luer lock, threaded coupling, or other suitable coupling, that is exposed when the stylet handle 114 is removed from the cannula handle 124. The coupling 126 can be configured to receive, for example, a syringe to aspirate or introduce fluids and/or other materials from or into the target location.

In some cases, the needle assembly may be difficult to maneuver and direct into the proper position and/or the needle assembly may be difficult for the user, such as a surgeon or other medical personnel, a surgical robot, or other surgical or stabilization device, to grasp. In some situations, the imaging equipment used to help guide the needle assembly may be in the user's way and restrict the user's ability to maneuver the needle assembly. In some cases, the user's hand may be exposed to ionizing radiation from the imaging equipment as the user is manipulating the needle assembly. Furthermore, in some procedures, the user may wish to drive the penetrating tip 116 into a boney target location, for example, to form a pilot hole or access bone marrow for a biopsy. To do so, the user may use a mallet or similar instrument to tap the stylet handle 114 and/or cannula handle 124. However, if the user must hold the needle assembly 100 and use a mallet on the needle assembly 100 itself, the user's hands may be in the way of imaging equipment and/or may be exposed to ionizing radiation from the imaging equipment.

Figure 2A:
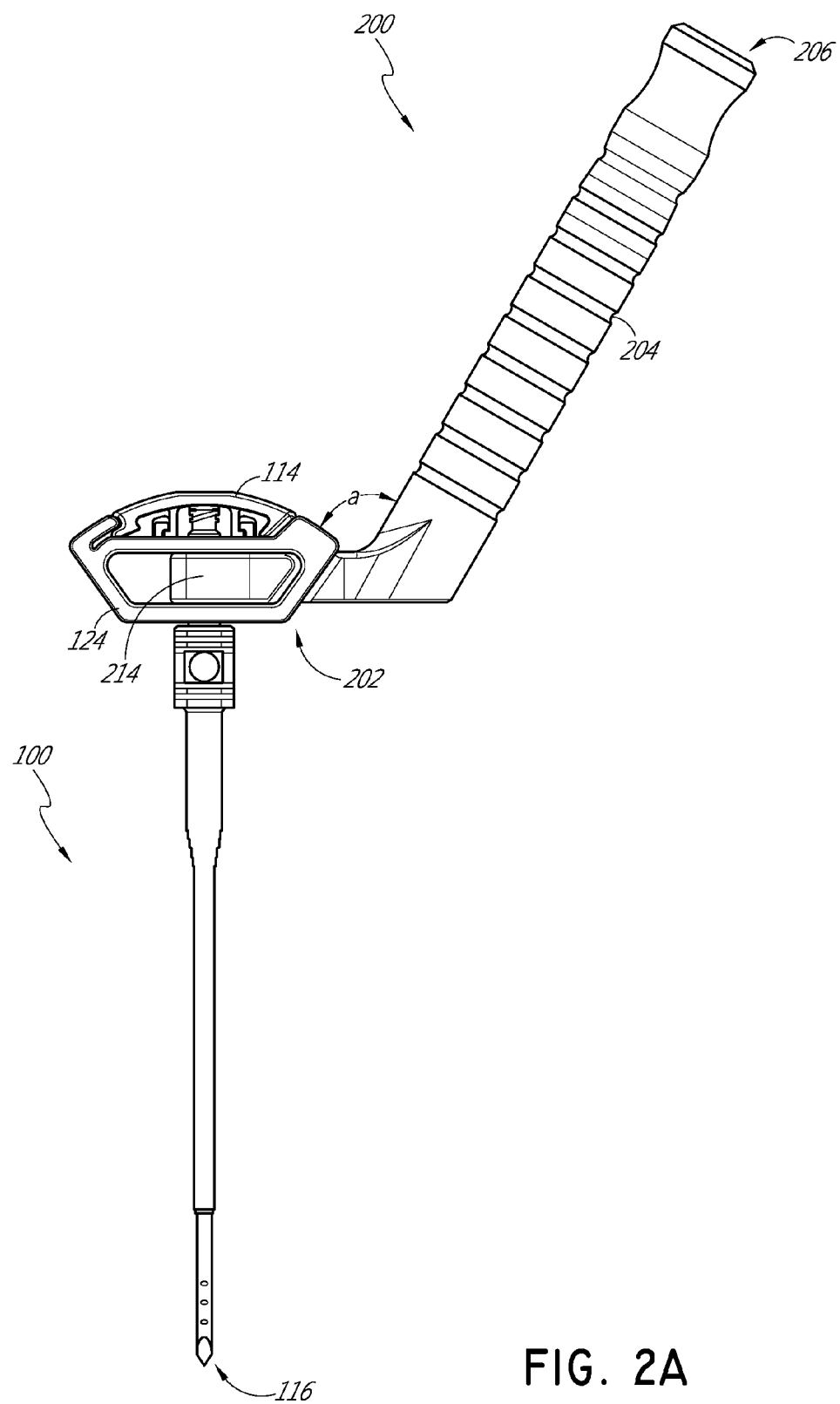
FIG. 2A illustrates a front view of an example embodiment of an impact handle coupled to a Jamshidi needle.
Figure 2B:
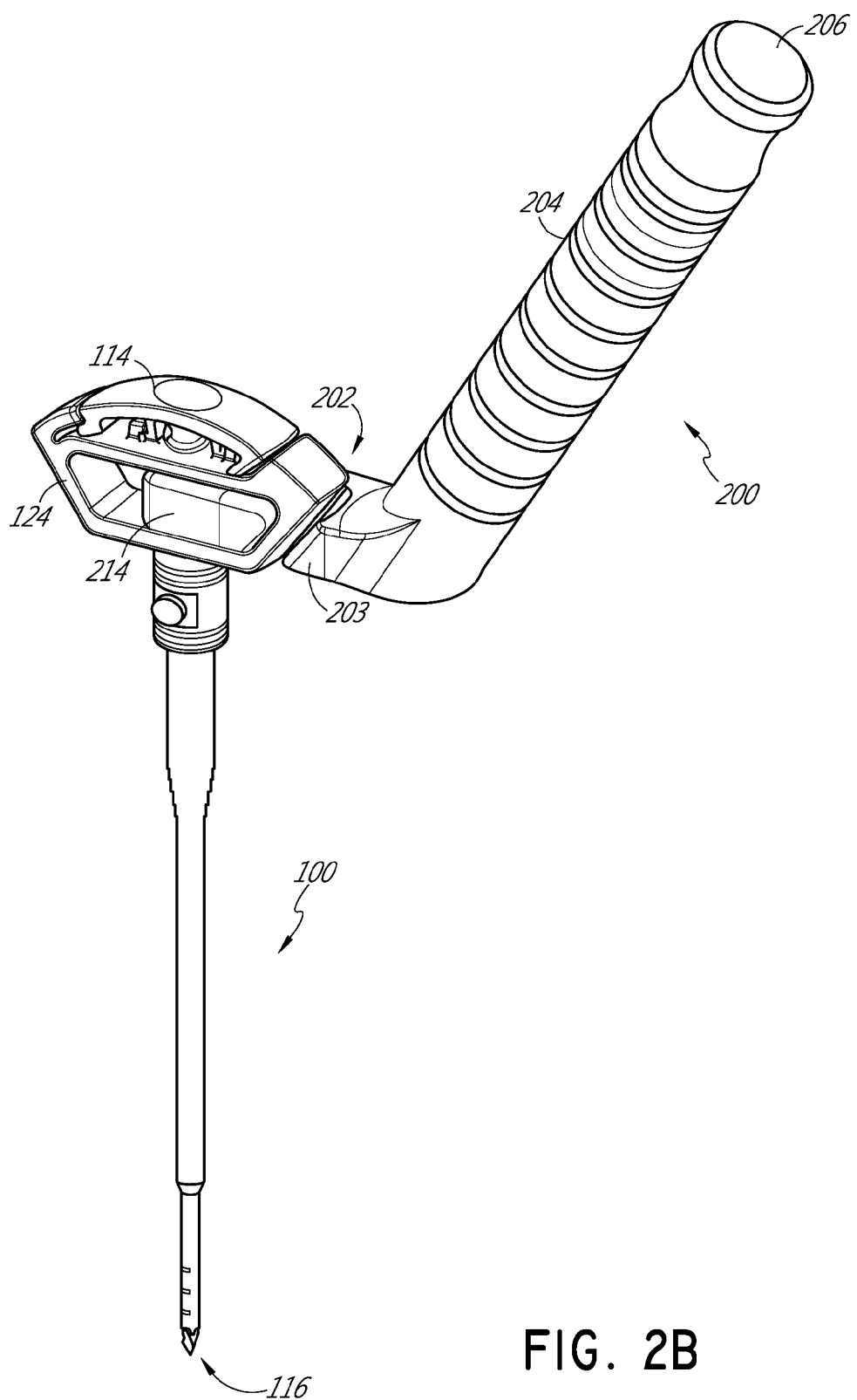
FIG. 2B illustrates a front perspective view of the impact handle coupled to the Jamshidi needle of FIG. 2A.

FIGS. 2A-2B illustrate an example embodiment of an impact handle or extension 200 coupled to a needle assembly. The impact handle 200, and other embodiments of impact handles shown and described herein, can be used with needle assembly 100 and/or other compatible needle assemblies. The impact handle 200 can be configured to attach to the cannula shaft 122 of the needle assembly and/or a handle of the needle assembly, for example, either or both of the stylet handle 114 and cannula handle 124. The impact handle 200 advantageously allows the user to, for example, maneuver, control the direction of, hold, and/or mallet the needle assembly 100 more easily and/or while keeping his or her hands away from the radiation and out of the way of imaging and/or other equipment. The impact handle 200 can also allow the user to maneuver or manipulate the needle assembly 100 as needed during the procedure. In some embodiments, the handle is radiolucent or at least partially radiolucent so that the handle does not obstruct images used to guide the procedure. For example, in some embodiments, the handle can be made of a plastic or composite material. In some embodiments, the handle can be disposable. Alternatively, the handle can be reusable.

As shown, the impact handle 200 includes an attachment portion 202 and a handle portion 204. The attachment portion 202 is configured to couple to the needle assembly 100. In the illustrated embodiment, the attachment portion 202 extends laterally away, or in a direction perpendicular or generally perpendicular to the stylet shaft 112 and cannula shaft 122 when the attachment portion 202 is coupled to the needle assembly 100. In some embodiments, for example as shown in FIGS. 2A and 2B, the handle portion 204 extends from the attachment portion 202 at an angle a. For example, the handle portion 204 can extend from the attachment portion 202 at an angle relative to vertical in the range of about 30° to about 60°, for example, about 45°. In the illustrated embodiment, the handle portion 204 is generally cylindrical, although other cross-sectional shapes are also possible. The handle portion 204 can include grooves, ridges, and/or other features configured to improve the user's grip on the handle portion 204. In some embodiments, a proximal end of the handle portion 204 can include an impact strikeplate 206. The impact strikeplate 206 provides a surface for tapping a mallet or similar instrument. In the illustrated embodiment, the impact strikeplate 206 is perpendicular to a longitudinal axis of the handle portion 204. The impact handle 200 can be configured to transfer forces from the impact strikeplate 206 to the needle assembly 100 to drive the penetrating tip 116 of the needle assembly 100 into the target bone. In some embodiments, the user can use a mallet or similar instrument directly on the needle assembly 100 or may not need or wish to use a mallet or similar instrument. In other words, the user does not need to use the impact strikeplate 206 and/or the impact handle 200 does not need to include an impact strikeplate 206 in some embodiments. If the user chooses to use the mallet or similar instrument directly on the needle assembly 100 or chooses not to use a mallet or similar instrument, the impact handle 200 still acts as an extension and allows the user to manipulate and hold the needle assembly 100 in position while keeping his or her hands out of or farther away from the radiation.

FIGS. 3A-3B illustrate another example embodiment of an impact handle 300 coupled to a needle assembly. This impact handle 300 also includes an attachment portion 302, a handle portion 304, and an impact strikeplate 306 at a proximal end of the handle portion 304. Surface 303 can also be used as an impact strikeplate, as discussed in greater detail herein. However, in the illustrated embodiment, the handle portion 304 is coupled to the attachment portion 302 via a curved intermediate portion 308. As shown, the attachment portion 302 extends generally laterally, horizontally, or perpendicularly to the stylet shaft 112 and cannula shaft 122 when coupled to the needle assembly 100, and a longitudinal axis of the handle portion 304 extends generally vertically and is oriented at about a 90° angle to the longitudinal axis of the attachment portion 302. Other angles and/or configurations are also possible.

Figure 4:
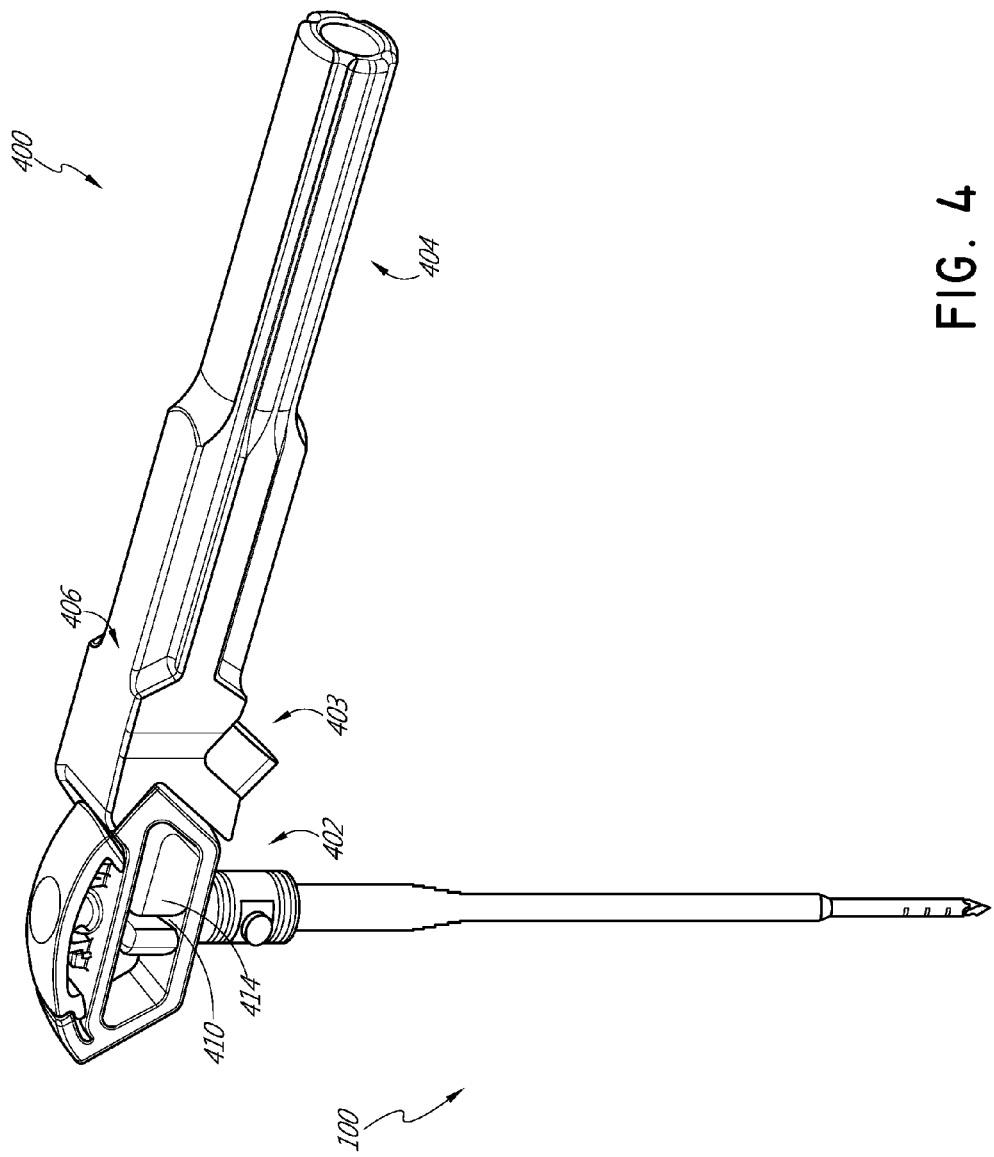
FIG. 4 illustrates a front perspective view of another example embodiment of an impact handle coupled to the Jamshidi needle.

FIG. 4 illustrates yet another example embodiment of an impact handle 400 coupled to a needle assembly. In the illustrated embodiment, the handle portion 404 extends linearly from the attachment portion 402. When the impact handle 400 is coupled to a needle assembly as shown, a longitudinal axis of the impact handle 400 extends generally perpendicularly to a longitudinal axis of the needle assembly. In the illustrated embodiment, the impact strikeplate 406 is positioned on a proximal surface of a body portion 403 of the impact handle 400 configured to be adjacent the handle of the needle assembly 100 in use.

Figure 5B:
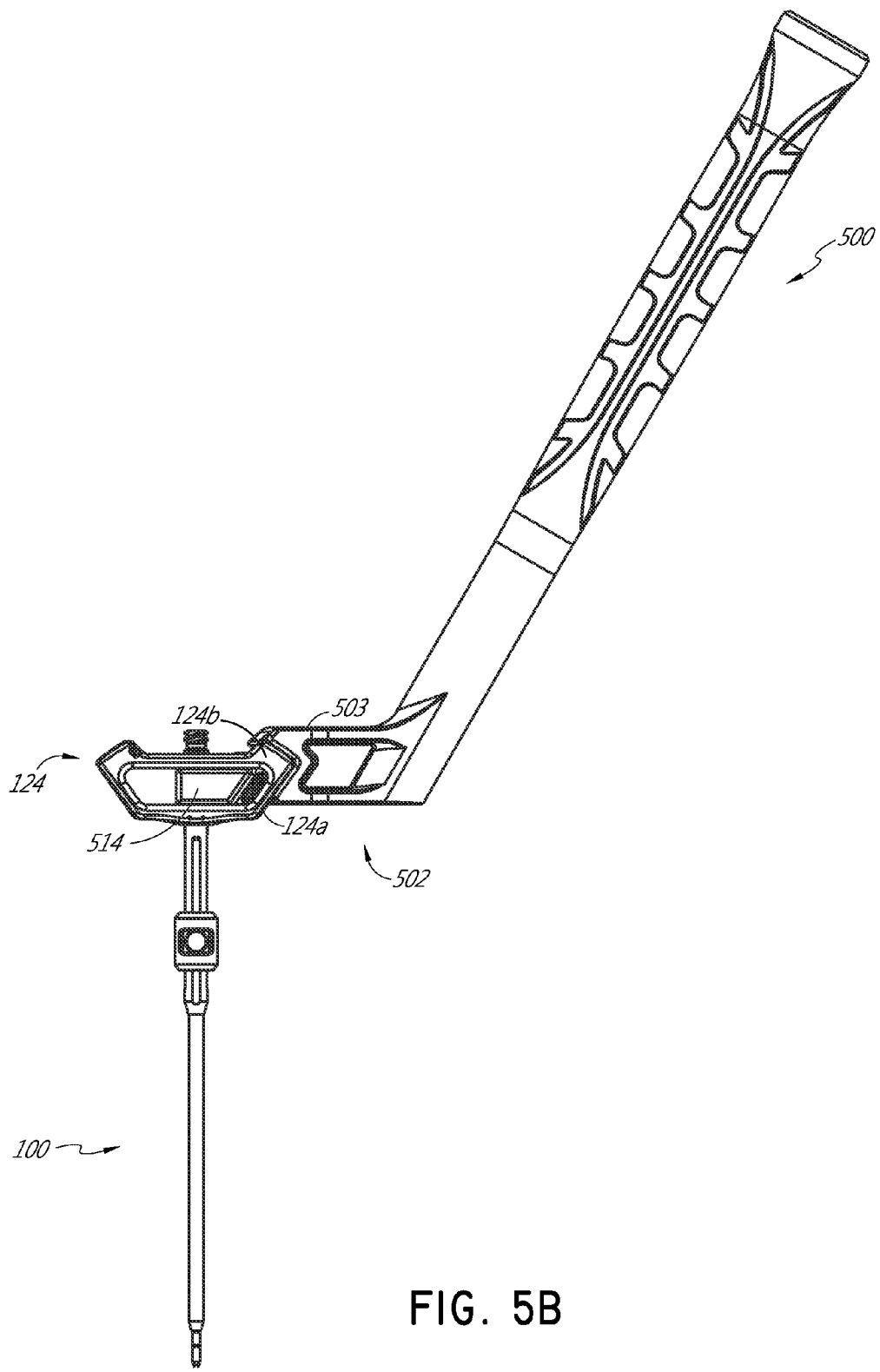
FIG. 5B illustrates a front view of the impact handle of FIG. 5A coupled to the Jamshidi needle.
Figure 5C:
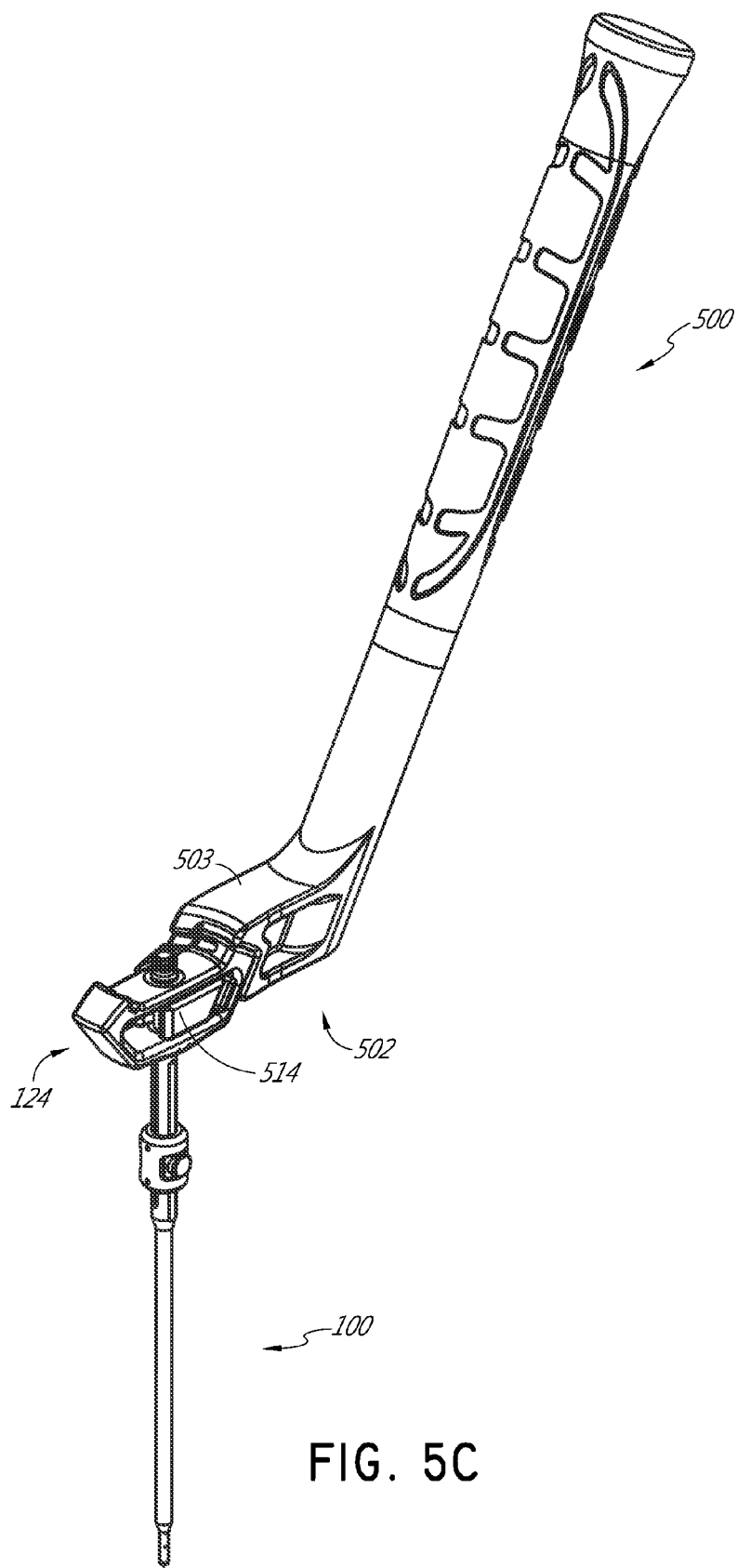
FIG. 5C illustrates a front perspective view of the impact handle of FIGS. 5A-5B coupled to the Jamshidi needle.

The attachment portion of the impact handle can include various mechanisms for connecting to the needle assembly. For example, the attachment portion can snap, twist, clip, or thread onto the needle assembly, or may couple to the needle assembly via any other suitable mechanism. FIGS. 5A-5C illustrate one example embodiment of an attachment portion 502 of an impact handle 500. In the illustrated embodiment, the attachment portion 502 includes a body portion 503, a sidewall 518 extending distally from the body portion 503, a connector 514 extending laterally from the sidewall 518, and a recess 516 bordered by the body portion 503, sidewall 518, and connector 514. The connector 514 includes a distal-facing notch 510 configured to engage the post 123 of the cannula shaft 122 extending through the cannula handle 124. The recess 516 is configured to receive a side 124a of the cannula handle 124. As shown in FIG. 5A, the handle 500 can approach the needle assembly at various angles from a front or back of the needle assembly to engage the notch 510 of the connector 514 with the post 123. The user can then turn or rotate the handle 500 to engage the recess 516 with the side 124a of the cannula handle 124 as shown in FIGS. 5B-5C. As shown, when the post 123 is fully seated in the notch 510 and the side 124a is fully seated in the recess 516, the connector 514 is substantially flush with the front of the cannula handle 124. The notch 510 and/or recess 516 can couple to the post 123 and/or side 124a, respectively, via, for example, a friction fit or snap fit.

Although FIGS. 5A-5C show the handle 500 approaching the needle assembly 100 from the back and the recess 516 engaging the right side of the cannula handle 124, the handle 500 could alternatively approach the needle assembly 100 from the front, and the recess 516 could engage the left side of the cannula handle 124. In the embodiment of FIGS. 5A-5C, the sidewall 518 and body portion 503 contact a proximal side portion 124b of the cannula handle 124 in addition to the side 124a. The attachment portion 302 of the impact handle 300 shown in FIGS. 3A and 3B has a similar configuration to attachment portion 502. The attachment portion 302 includes a body portion 303, connector 314, sidewall 318, notch, and recess, and the body portion 303 and sidewall 318 contact both the side 124a and proximal side portion 124b of the cannula handle 124. The attachment portion 202 of the impact handle 200 shown in FIGS. 2A and 2B is also similar and includes a body portion 203, connector 214, sidewall, notch, and recess, but the body portion 203 and sidewall do not contact the proximal side portion 124b of the cannula handle 124. The attachment portion 402 of the impact handle 400 shown in FIG. 4 also includes a similar connector 414. However, as shown, the notch 410 is lateral-facing rather than distal-facing relative to the impact handle 400 so that the notch 410 faces forward when the handle 400 is coupled to the needle assembly 100. The handle 400 can be coupled to the needle assembly 100 by sliding or snapping the notch 410 onto the post 123 and the recess onto the cannula handle 124 from the front or back of the needle assembly 100.

Figure 6C:
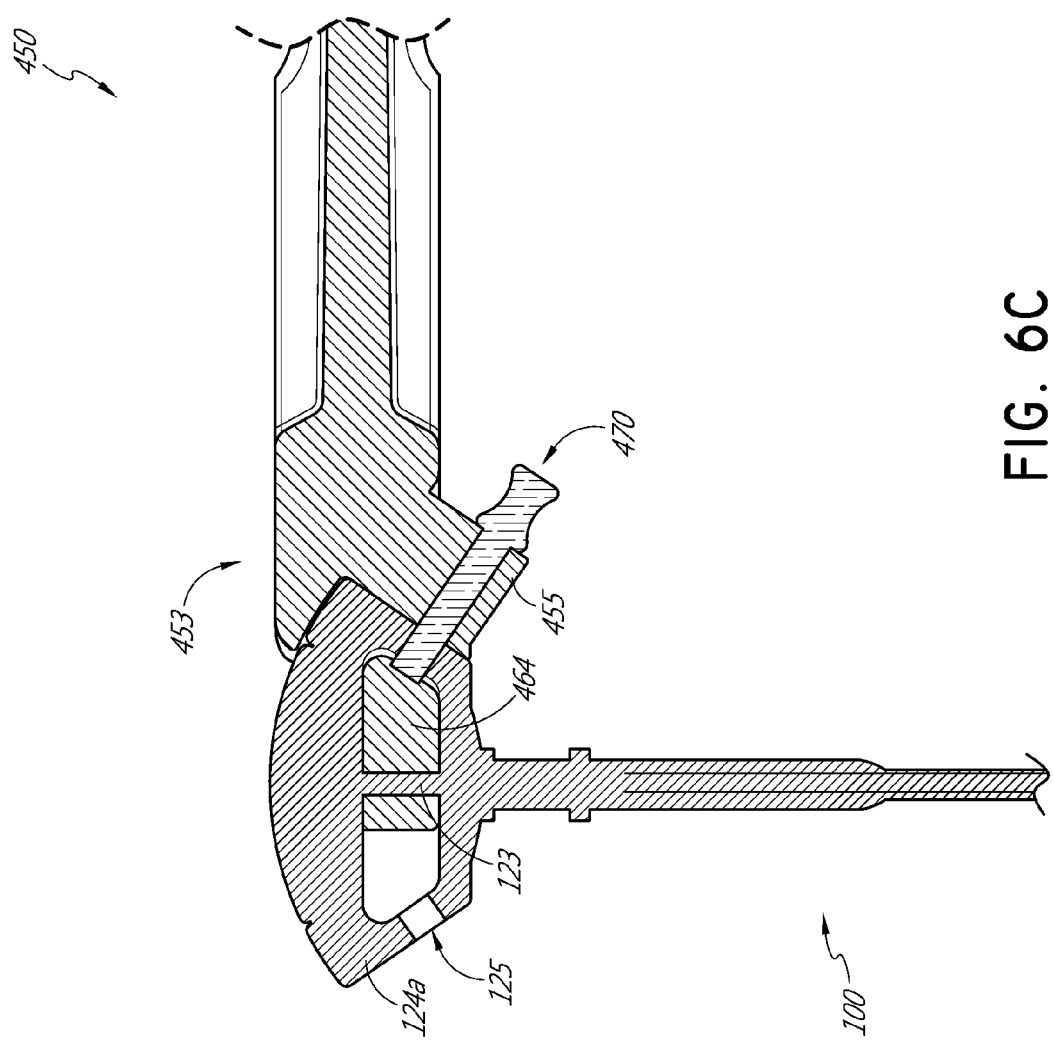
FIG. 6C illustrates a section view of the impact handle coupled to the Jamshidi needle of FIG. 6B.

FIGS. 6A-6C illustrate an impact handle 450 similar to impact handle 400 shown in FIG. 4. The attachment portion 452 is similar to attachment portion 402. However, as shown, attachment portion 452 also includes a spring-loaded pin 470. The pin 470 can advantageously help secure the attachment portion 452 to the needle assembly 100. In the illustrated embodiment, the bottom of the body portion 453 of the impact handle 450 includes a protrusion 455. The pin 470 extends through the protrusion 455 and an upward, diagonal angle. In some embodiments, one or both sides 124a of the cannula handle 124 can include an aperture 125 configured to receive the pin 470, as shown in FIGS. 6A and 6C. To couple the attachment portion 452 to the needle assembly, the user can retract or pull back on the pin 470 as shown in FIG. 6A to couple the notch 460 to the post 123 and the recess 466 to the side 124a of the cannula handle 124. The user can then release the pin 470 so that the pin 470 extends through the protrusion 455 and side 124a of the cannula handle 124 to contact the connector 464 as shown in FIGS. 6B-6C. In some embodiments, the pin 470 can also or alternatively include a threaded portion configured to engage a corresponding threaded portion in the protrusion 455.

Figure 7A:
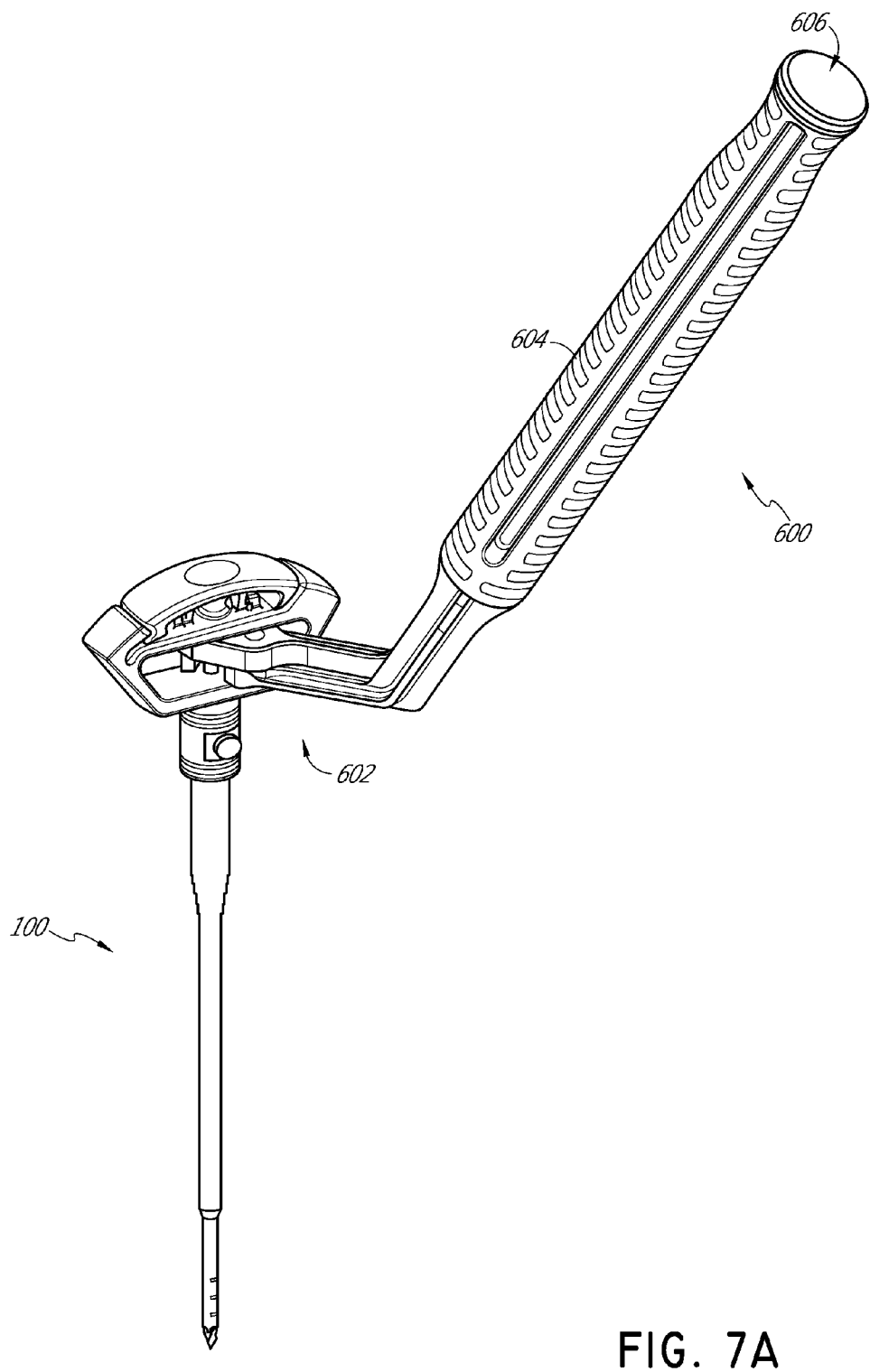
FIG. 7A illustrates a front perspective view of another example embodiment of an impact handle coupled to the Jamshidi needle.
Figure 7B:
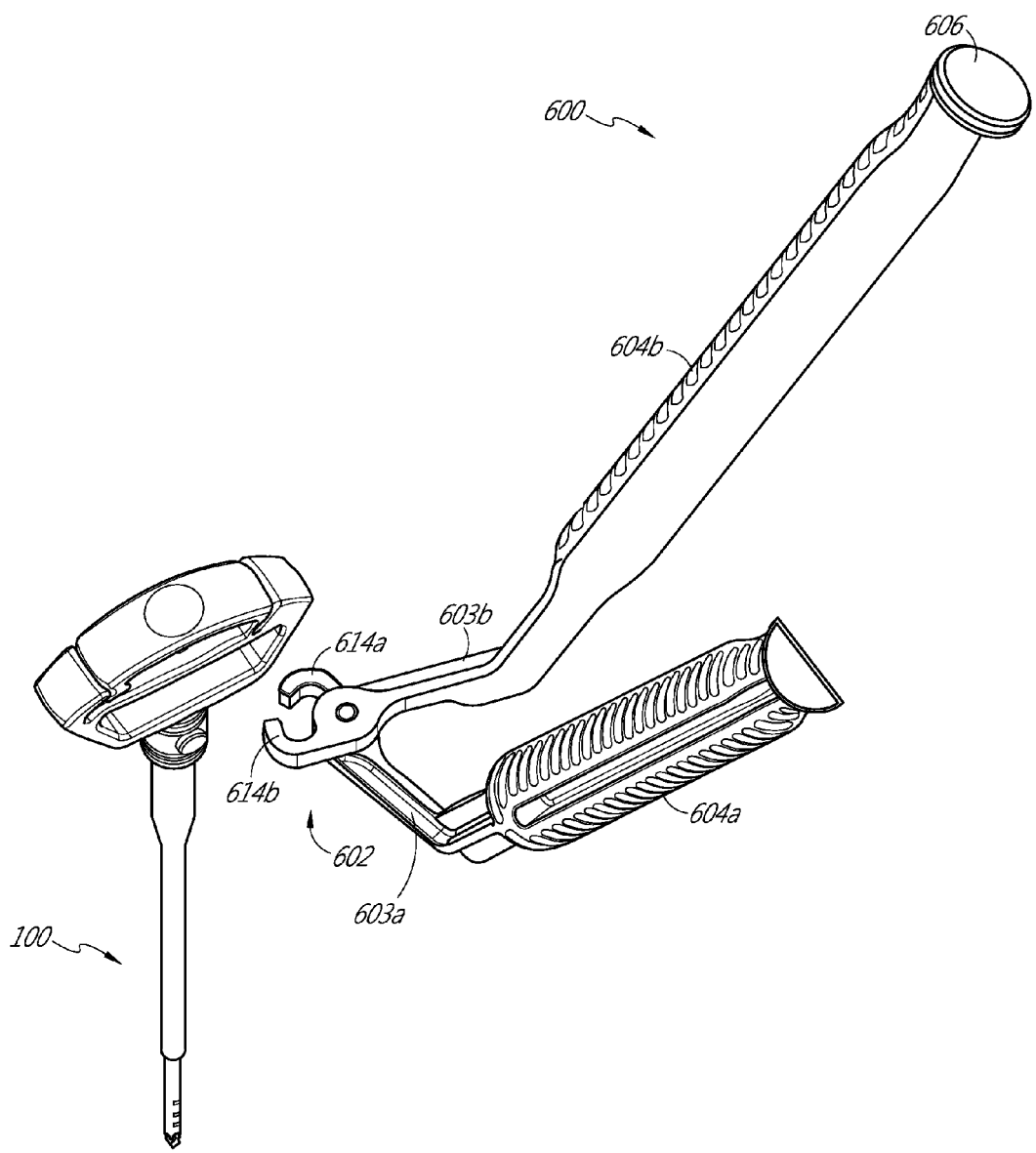
FIG. 7B illustrates the impact handle of FIG. 7A before being coupled to the Jamshidi needle.
Figure 7C:
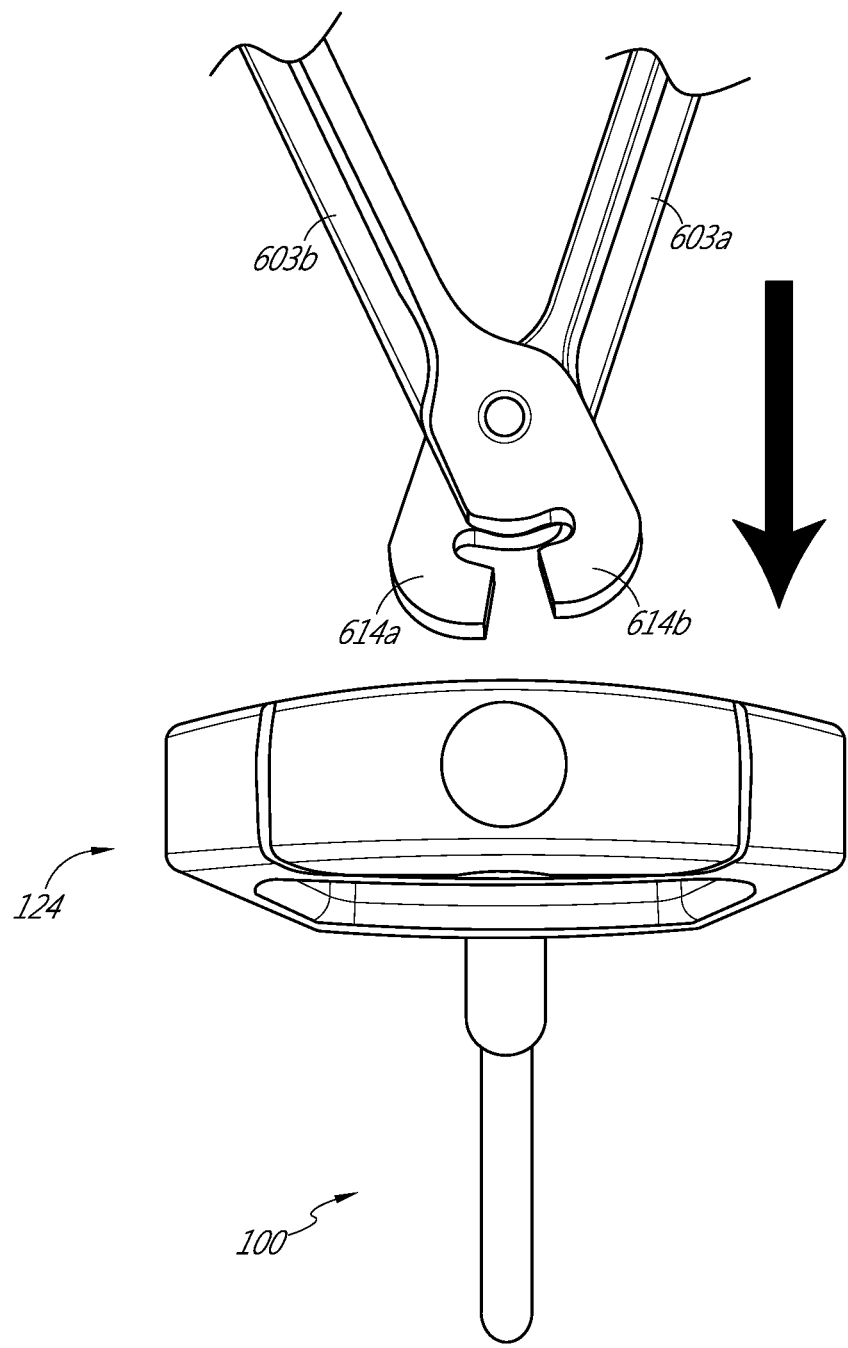
FIG. 7C illustrates a partial top perspective view of the impact handle of FIGS. 7A-7B before being coupled to the Jamshidi needle.
Figure 7D:
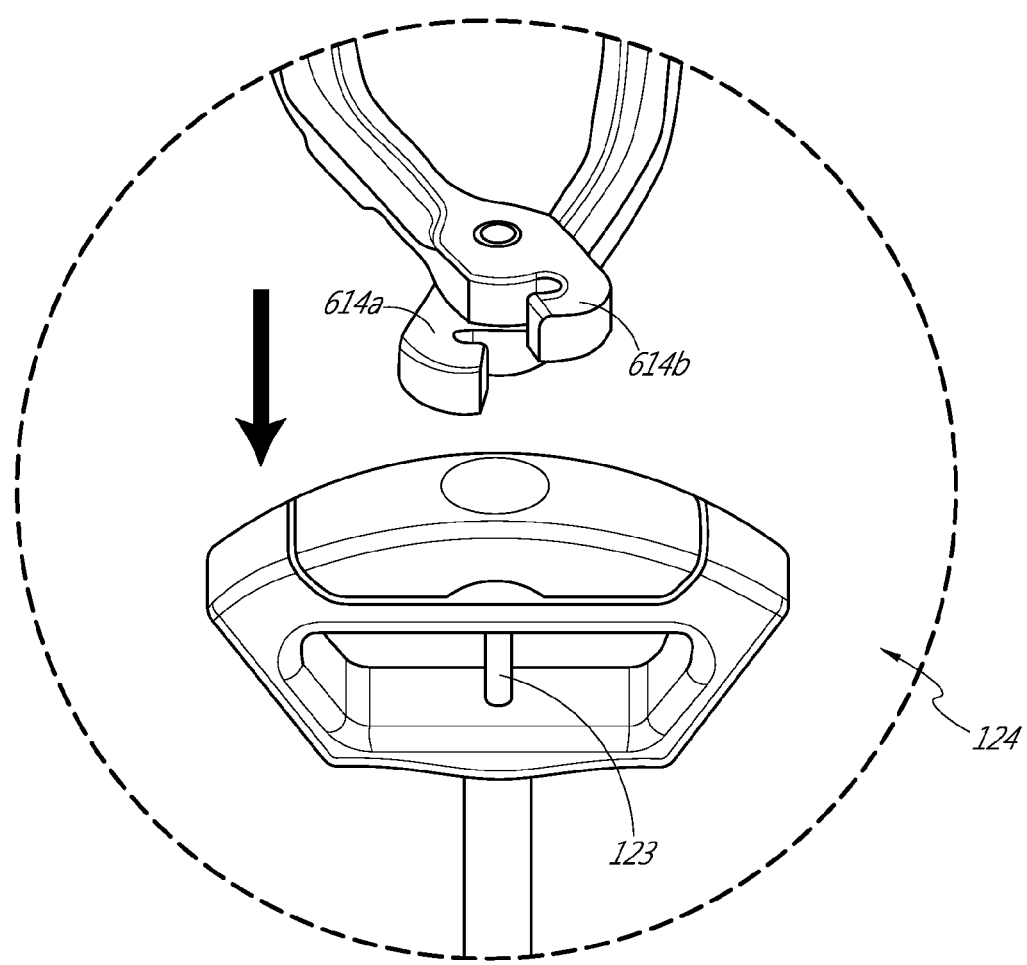
FIG. 7D illustrates another partial top perspective view of the impact handle of FIGS. 7A-7C before being coupled to the Jamshidi needle.
Figure 7E:
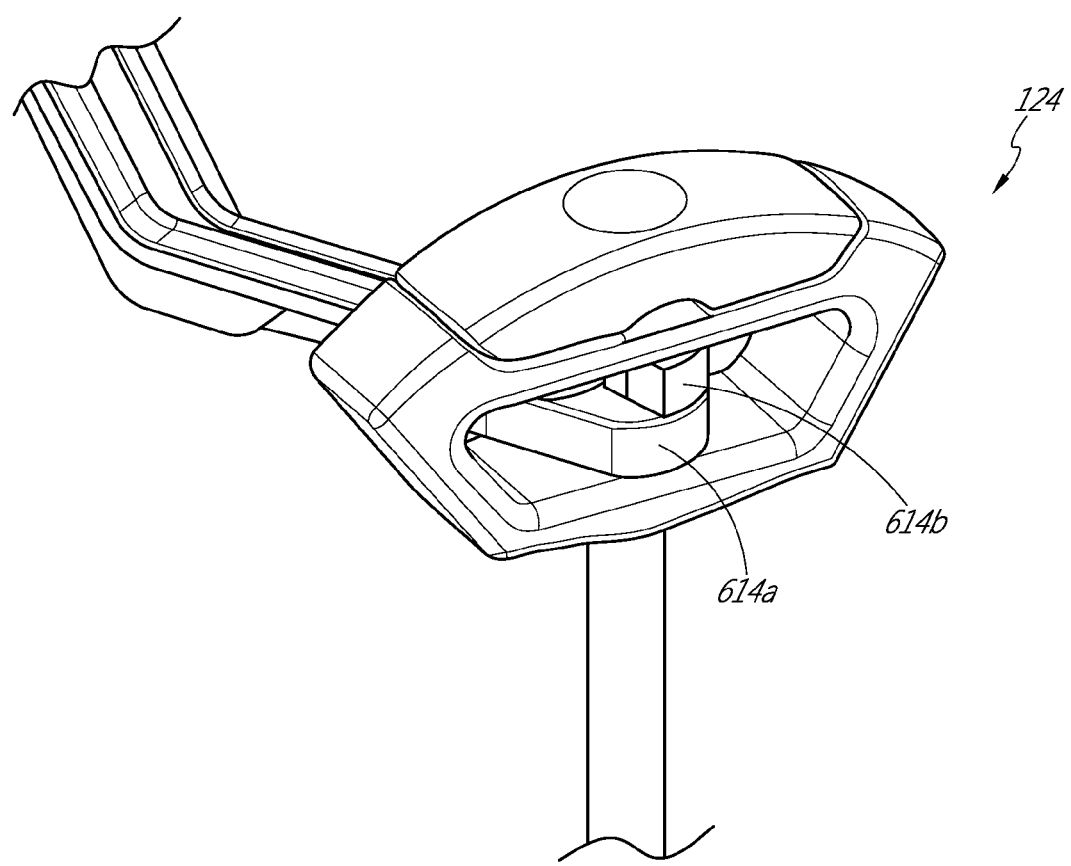
FIG. 7E illustrates a partial front perspective view of the impact handle of FIGS. 7A-7D coupled to the Jamshidi needle.

The attachment portion 602 of the impact handle 600 illustrated in FIGS. 7A-7E includes a Kocher or clamp style attachment mechanism. As shown, the handle portion 604 can include two halves 604a and 604b. In the illustrated embodiment, the impact strikeplate 606 is located on a proximal end of one half 604b of the handle portion 604. However, the impact strikeplate 606 can also be located on a proximal end of the other half 604a of the handle portion 604, or each half 604a and 604b of the handle portion 604 can include a portion of the impact strikeplate 606. The body portion 603 of the impact handle 600 can also include two halves 603a and 603b, each having a curved clamp portion 614a and 614b, respectively, at a distal end. The user can separate the halves 604a and 604b of the handle portion 604 to open the clamp portions 614a and 614b as shown in FIGS. 7B-7D. The user can then close the clamp portions 614a and 614b around the post 123 of the cannula shaft 122 extending through the cannula handle 124 as shown in FIGS. 7A and 7E. In the illustrated embodiment, the clamp portion 614b is partially stacked on top of clamp portion 614a when the clamp portions 614a and 614b are closed around the post 123.

Figure 8A:
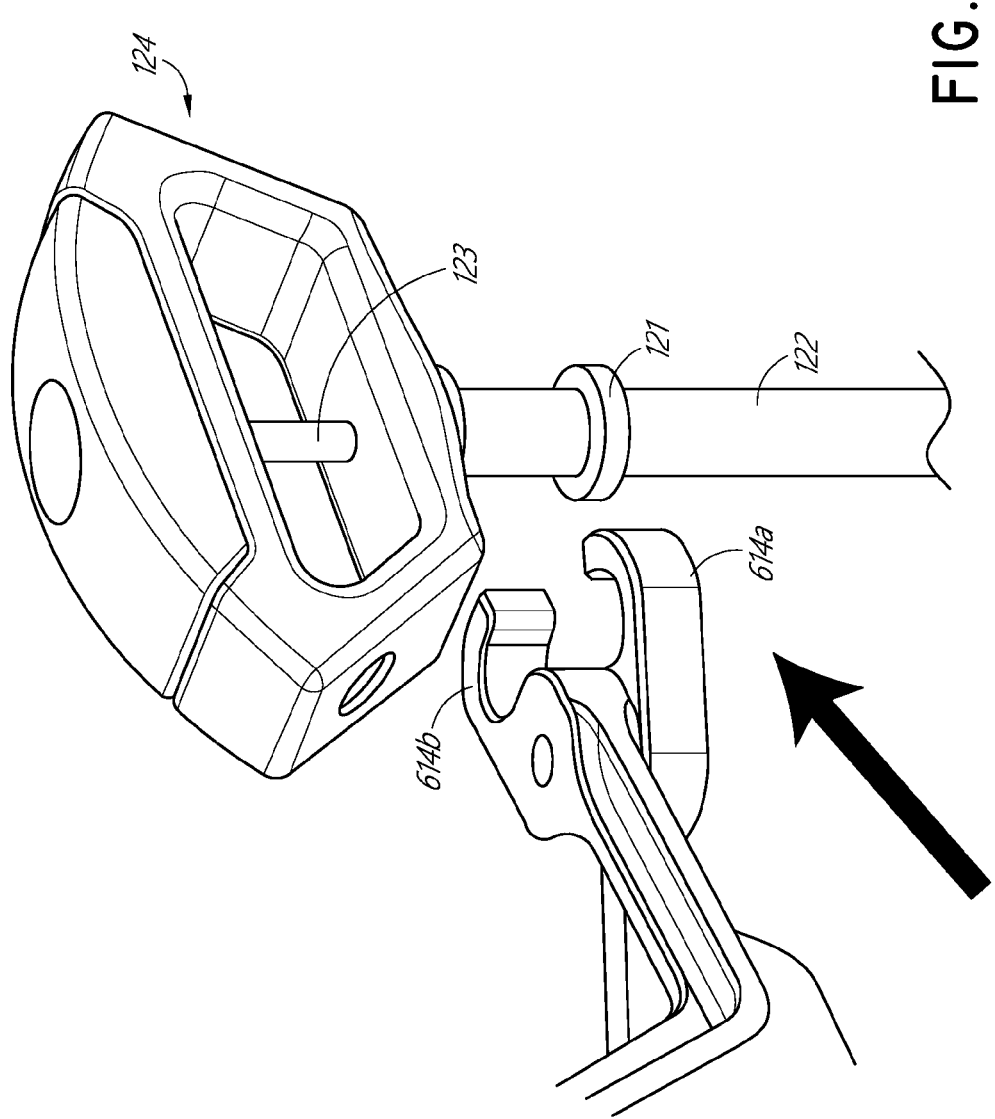
FIG. 8A illustrates a partial front perspective view of the impact handle of FIGS. 7A-7E before being coupled to another portion of the Jamshidi needle.
Figure 8B:
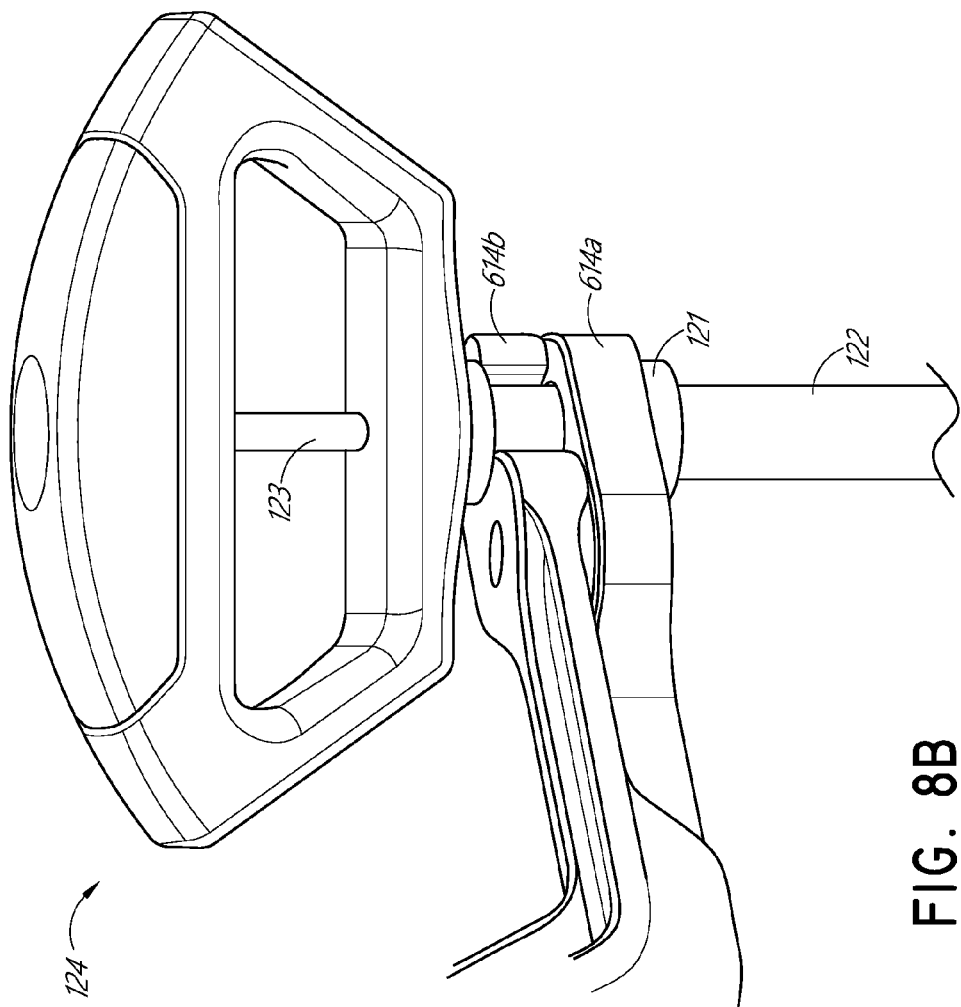
FIG. 8B illustrates a partial front view of the impact handle of FIGS. 7A-8A coupled to the other portion of the Jamshidi needle.

Although the attachment portions 202, 302, 402, 452, 502, and 602 shown in FIGS. 2A-7E couple to the post 123 of the cannula shaft 122 extending through the cannula handle 124, impact handles according to the present disclosure can include attachment portions that couple to another portion of the cannula shaft 122. For example, FIGS. 8A-8B illustrate the Kocher or clamp style attachment portion 602 coupled to the cannula shaft 122 distal to the cannula handle 124 rather than to the post 123. In some embodiments, for example as shown in FIGS. 8A-8B, a ring 121 can be placed on the cannula shaft 122 to help guide placement of the clamp portions 614a, 614b on the cannula shaft 122 and/or to help inhibit the clamp portions 614a, 614b from sliding on the cannula shaft 122.

Figure 9A:
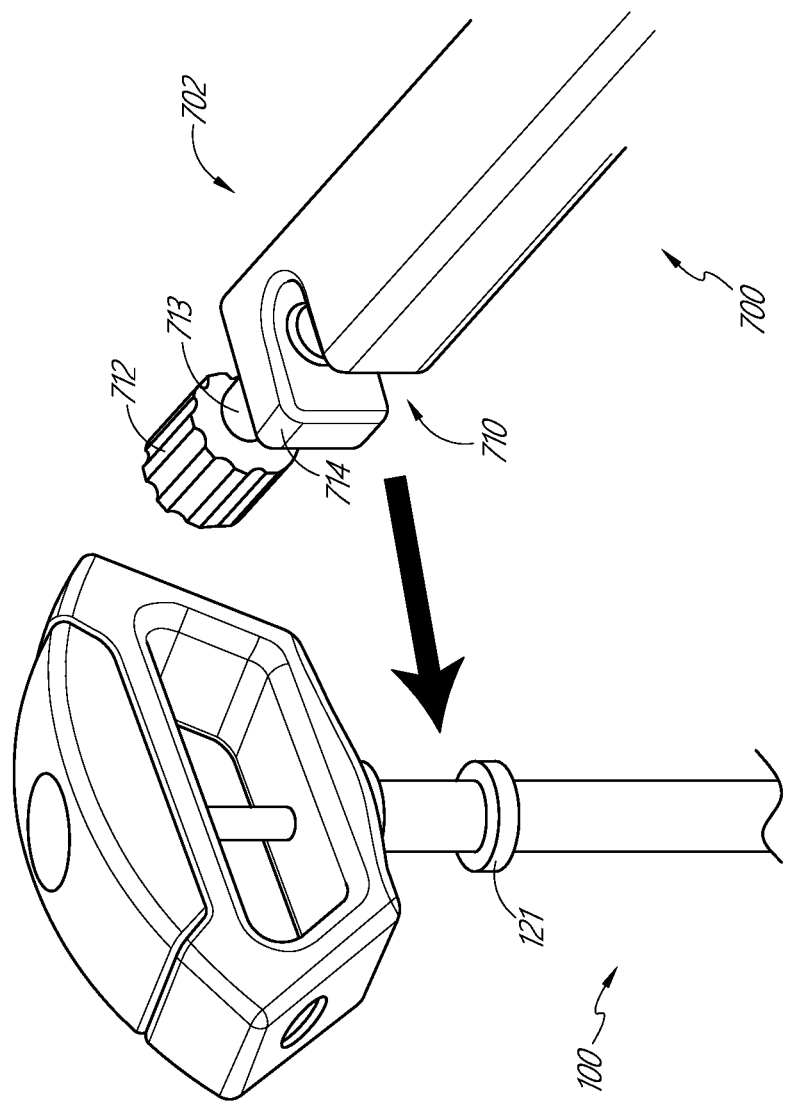
FIG. 9A illustrates a partial front perspective view of another example embodiment of an impact handle before being coupled to a Jamshidi needle.
Figure 9B:
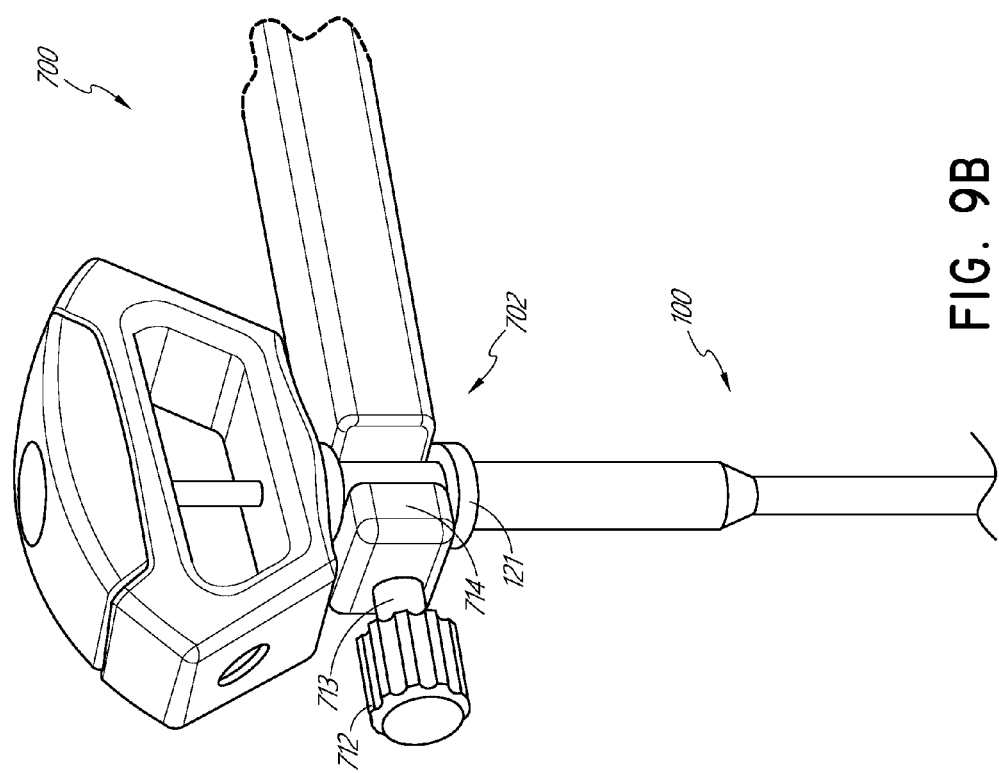
FIG. 9B illustrates a partial front perspective view of the impact handle of FIG. 9A coupled to the Jamshidi needle.

FIGS. 9A-9B illustrate another example embodiment of an impact handle 700 having an attachment portion 702 coupled to the cannula shaft 122 distal to the cannula handle 124. The attachment portion 702 includes a lateral-facing notch 710, a distal wall 714 between the notch 710 and distal end of the impact handle, a pin 713 extending through the distal wall 714, and a knob 712 at a distal end of the pin 713. The notch 710 is configured to slide onto the cannula shaft 122, and the pin 713 is configured to clamp or secure the attachment portion 702 to the cannula shaft 122. In some embodiments, the pin 713 includes screw threads configured to engage corresponding screw threads in the distal wall 714. The user can rotate the knob to tighten the pin 713 on the cannula shaft or loosen the pin 713 from the cannula shaft. In other embodiments, the pin 713 can be spring-loaded. The user can pull the knob 712, and therefore the pin 713, away from the distal wall 714 to fit the cannula shaft 122 into the notch 710, then release the knob 712 to allow the pin 713 to engage the cannula shaft 122 and secure the attachment portion 702 to the cannula shaft 122. In the illustrated embodiment, the cannula shaft 122 includes a ring 121 to help guide placement of the attachment portion 702 on the cannula shaft 122 and/or to help inhibit the attachment portion 702 from sliding on the cannula shaft 122.

Figure 10A:
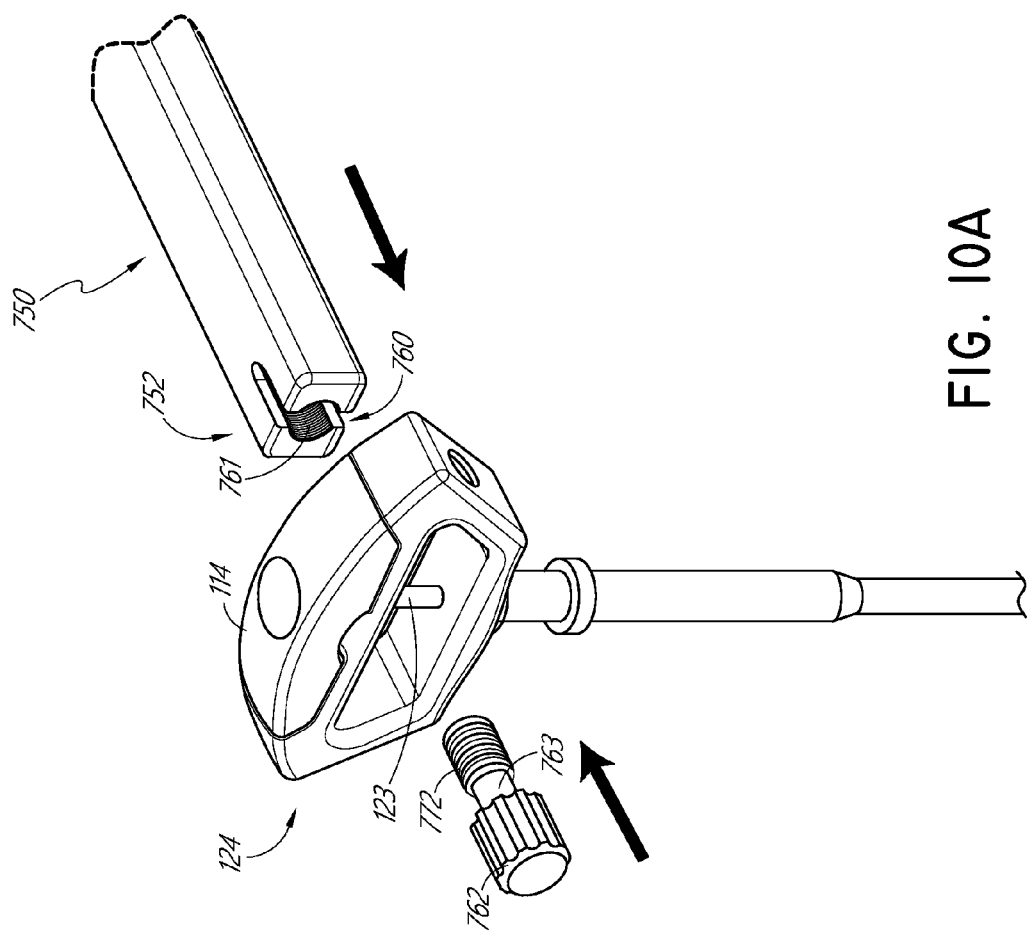
FIG. 10A illustrates a partial front perspective view of another example embodiment of an impact handle before being coupled to a Jamshidi needle.
Figure 10B:
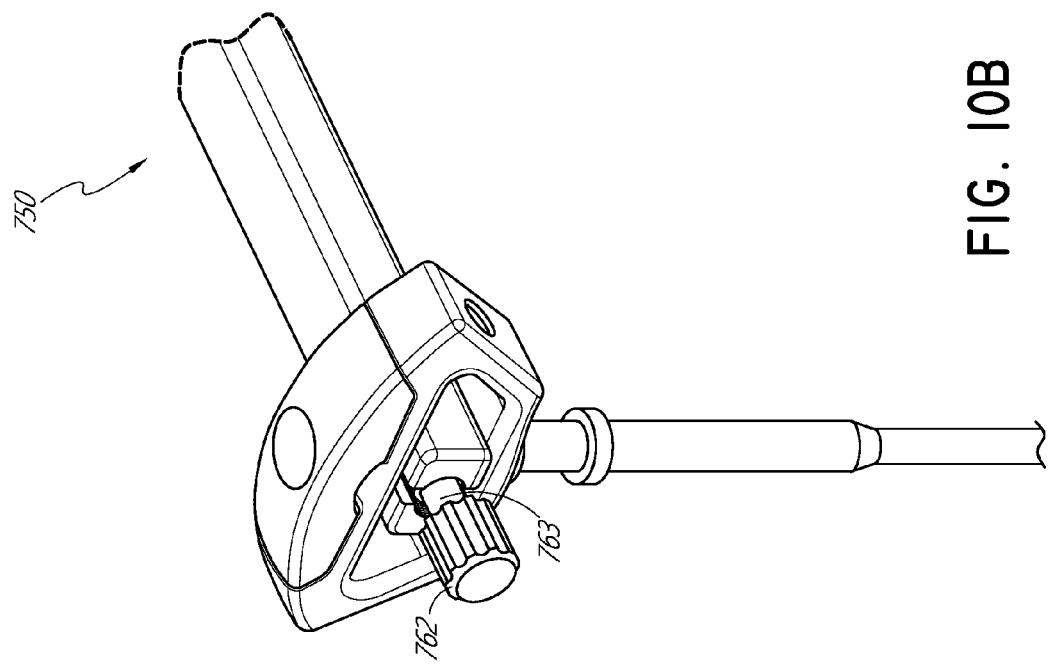
FIG. 10B illustrates a partial front perspective view of the impact handle of FIG. 10A coupled to the Jamshidi needle.

As shown in FIGS. 10A-10B, an impact handle 750 having an attachment portion 752 having a pin 763 and a knob 762 can also be configured to couple to the post 123 of the cannula shaft 122 extending through the cannula handle 124. In the illustrated embodiment, the notch 760 opens to the distal end of the attachment portion 752, and the pin 763 is configured to extend into the notch 760 from the open distal end. In this embodiment, the pin 763 includes exterior threads 772 configured to mate with interior threads 761 in the notch 760. In use, the user can slide the notch 760 onto the post 123, then thread the pin 763 into the notch 760 to secure the attachment portion 752 to the needle assembly. The attachment portion 752 of FIGS. 10A-10B could also be configured to be secured to a portion of the cannula shaft 122 distal to the cannula handle 124.

In some embodiments, the attachment portion of an impact handle can include a locking cam to help secure the impact handle to the needle assembly. For example, the impact handle 800 shown in FIGS. 11A-11E includes an attachment mechanism similar to the connector-style attachment mechanism shown in FIGS. 5A-5C and described herein with some modifications. As shown, the attachment portion 802 includes a sidewall 818 and a connector 814 having a distal-facing notch 810. The attachment portion 802 includes a locking cam 820. A first end 820a of the locking cam 820 is pivotally coupled to the body portion 803 of the attachment portion 802. In use, a free end 820b of the locking cam 820 is rotated between a horizontal position adjacent the body portion 803 and a substantially vertical position. In some embodiments, the horizontal position is a locked position and the vertical position is an unlocked position. In other embodiments, the horizontal position is an unlocked position and the vertical position is a locked position.

Figure 11A:
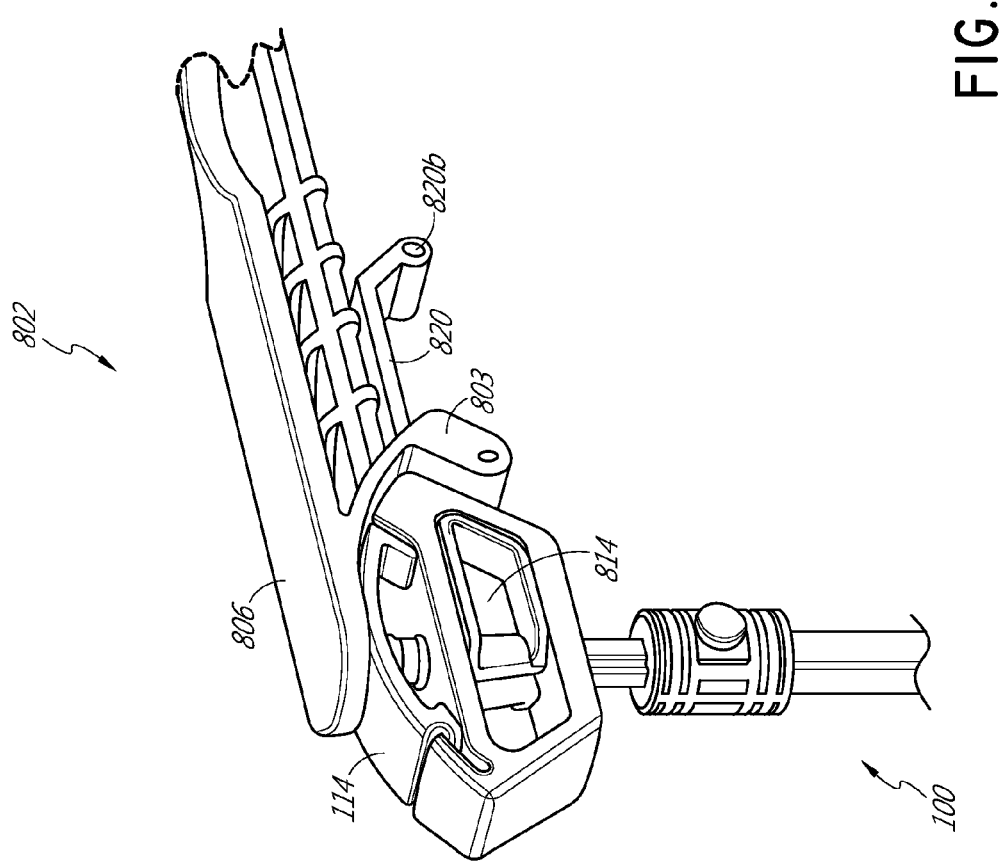
FIG. 11A illustrates a partial front perspective view of another example embodiment of an impact handle coupled to a Jamshidi needle.
Figure 11B:
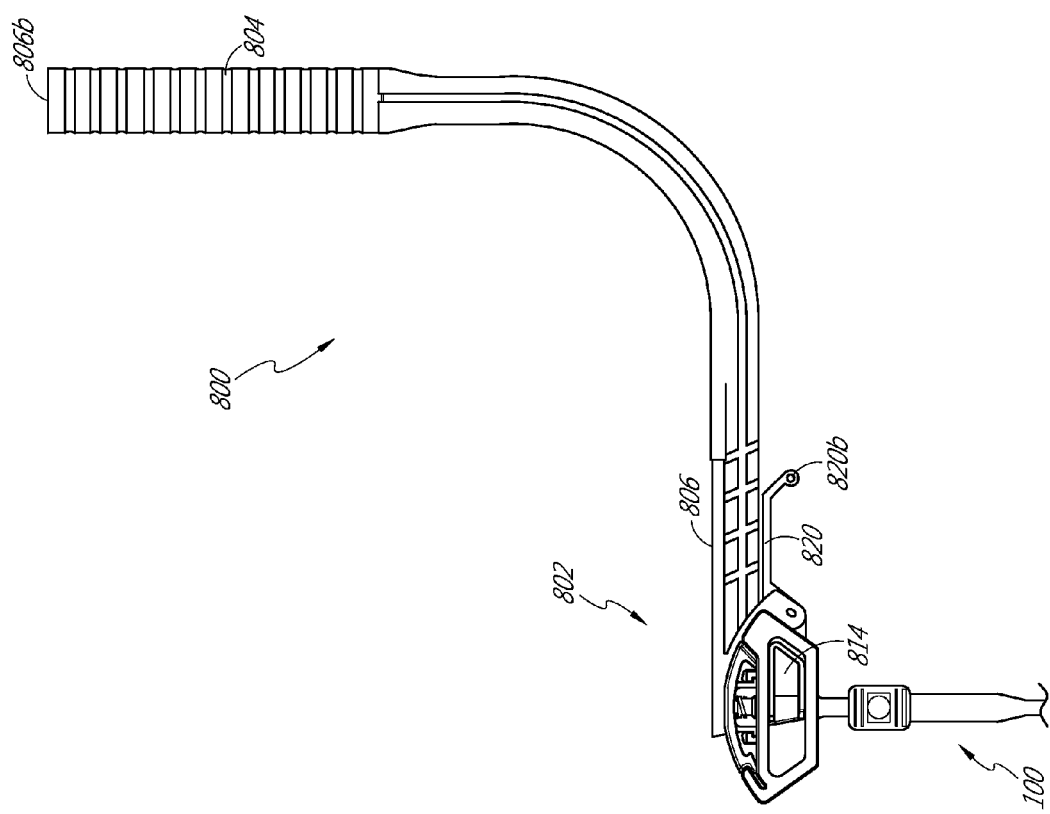
FIG. 11B illustrates a front view of the impact handle of FIG. 11A coupled to the Jamshidi needle.
Figure 11D:
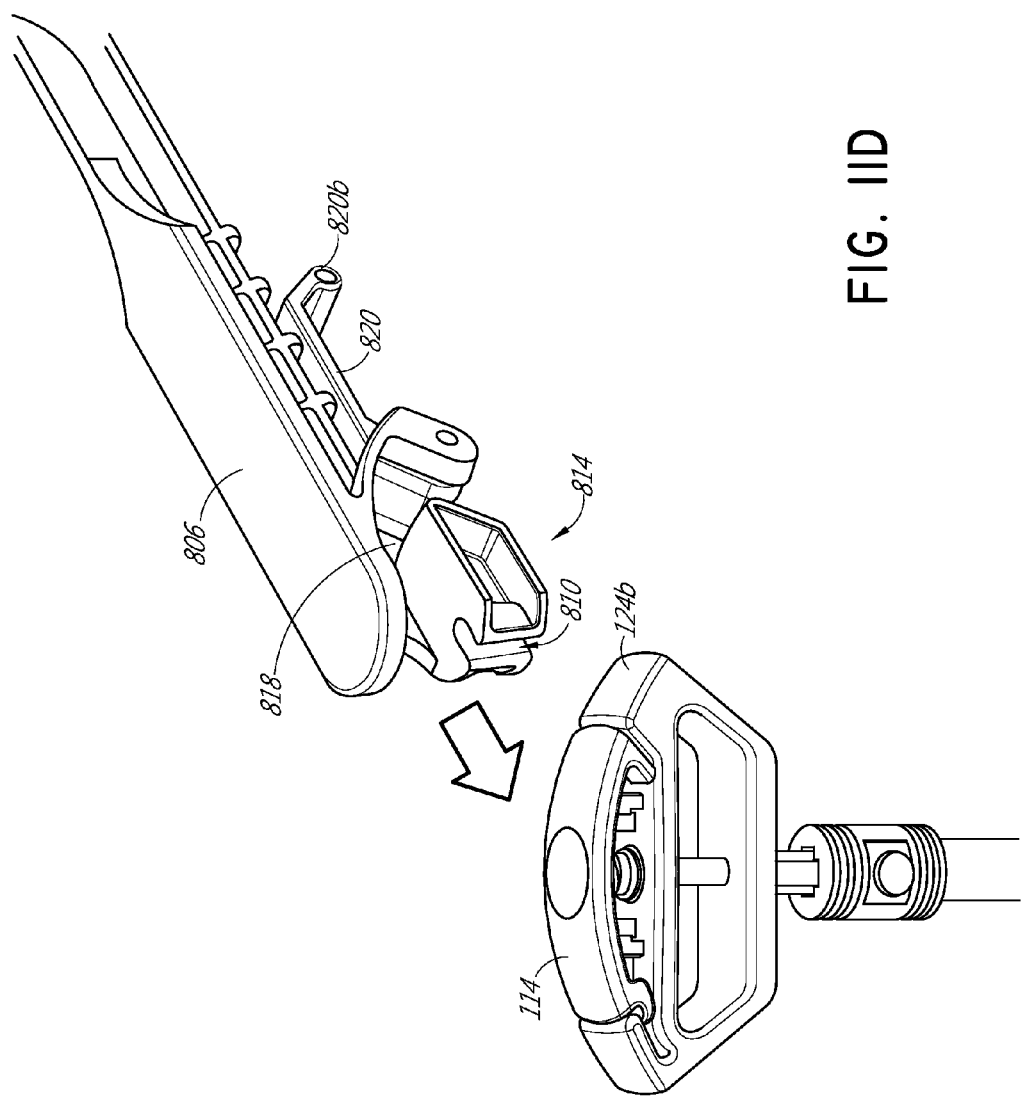
FIG. 11D illustrates a partial top perspective view of the impact handle of FIGS. 11A-11C before being coupled to the Jamshidi needle.
Figure 11E:
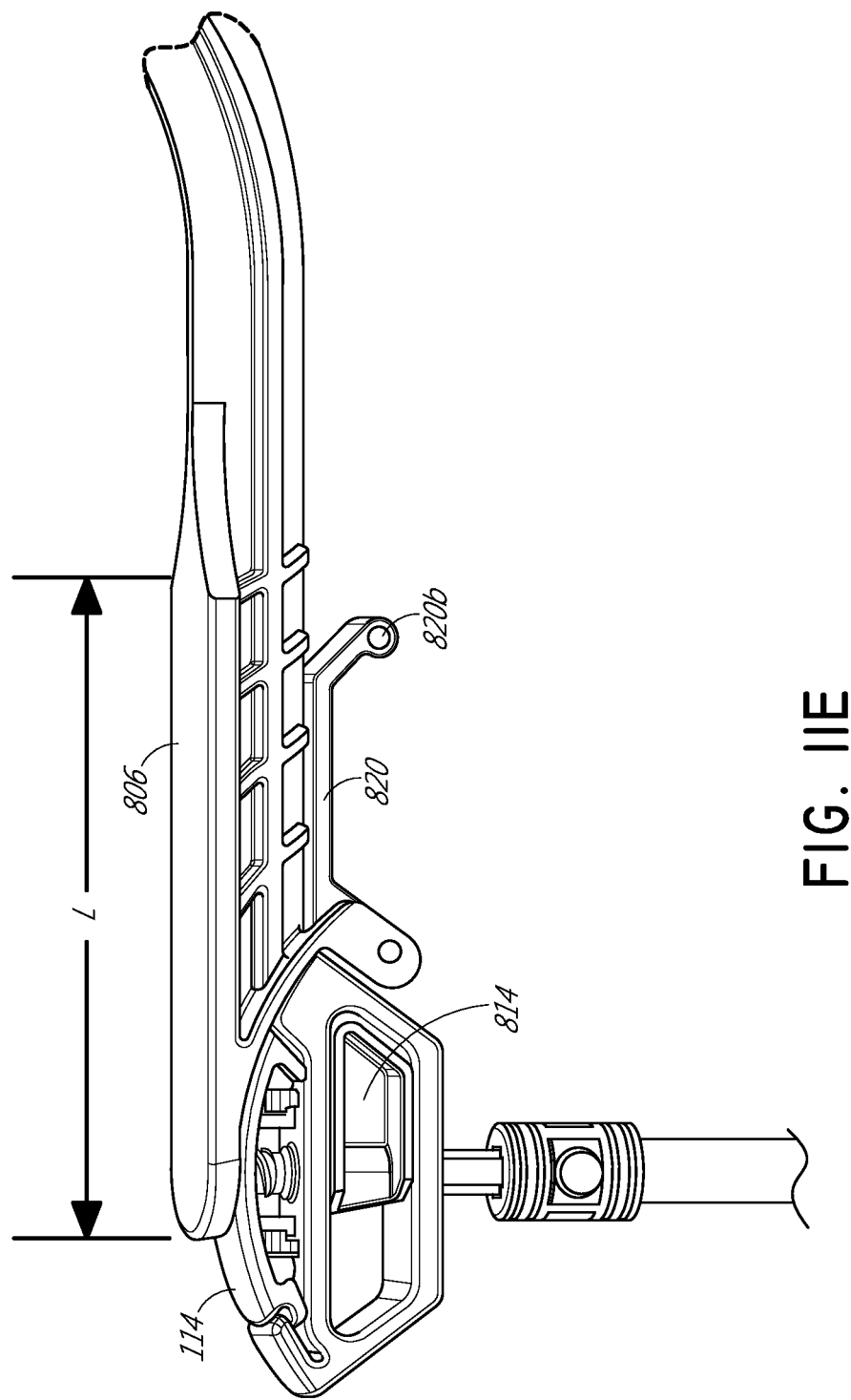
FIG. 11E illustrates a partial front view of the impact handle of FIGS. 11A-11D coupled to the Jamshidi needle.
Figure 11F:
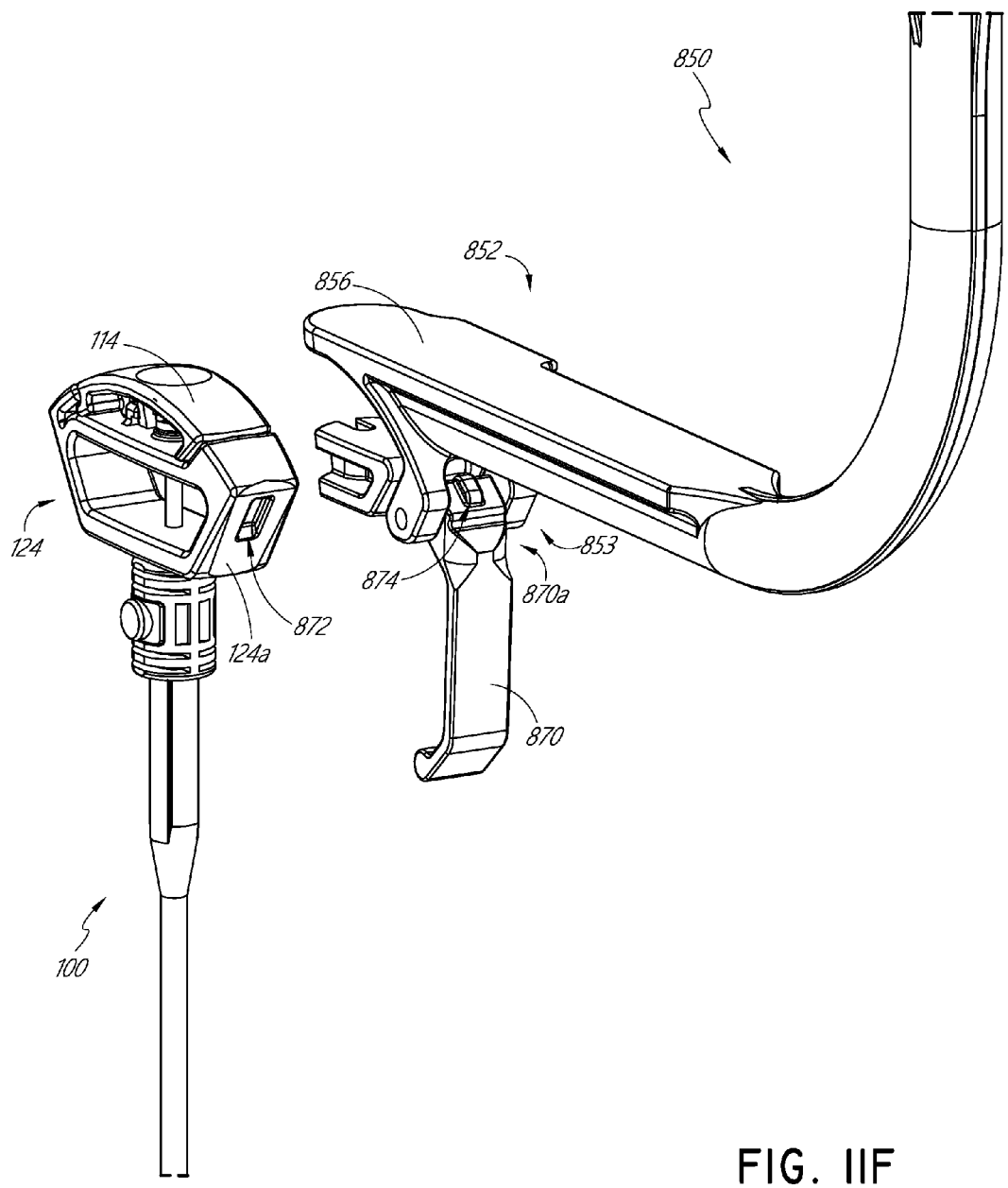
FIG. 11F illustrates a partial perspective view of another example embodiment of an impact handle before being coupled to a Jamshidi needle.
Figure 11G:
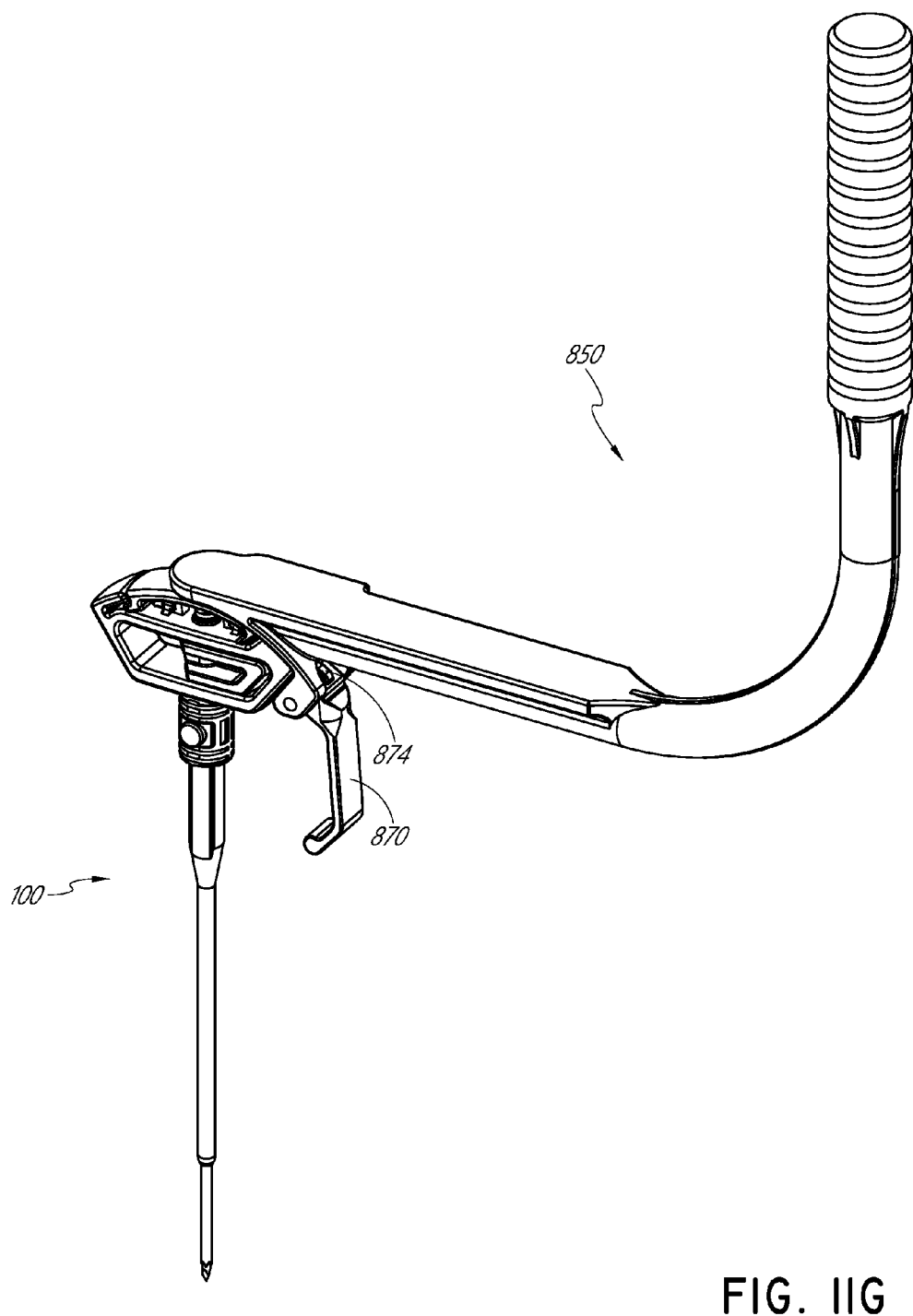
FIG. 11G illustrates a perspective view of the impact handle of FIG. 11F coupled to the Jamshidi needle in an unlocked position.
Figure 11H:
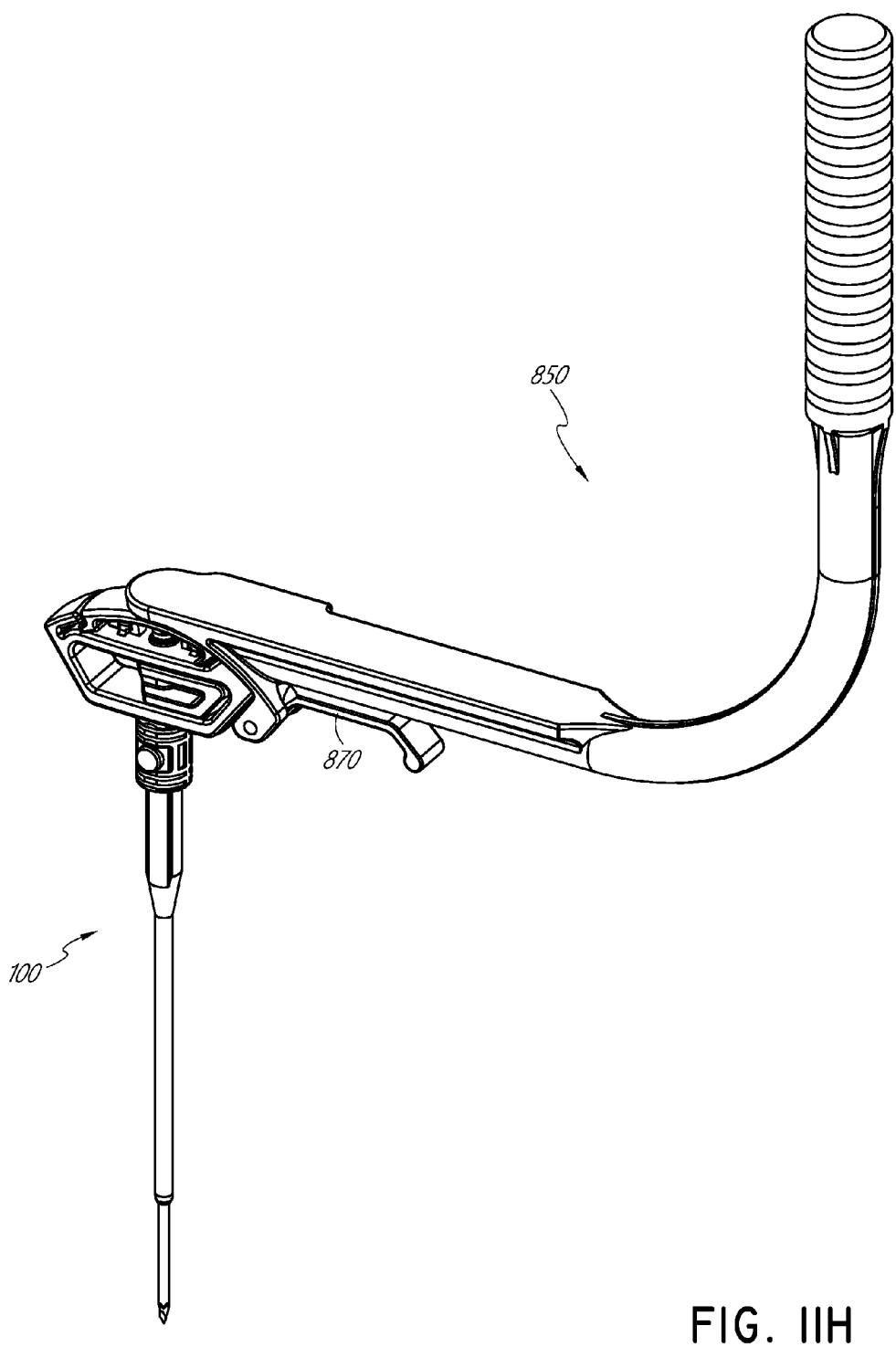
FIG. 11H illustrates a perspective view of the impact handle of FIGS. 11F-11G coupled to the Jamshidi needle in a locked position.
Figure 111:
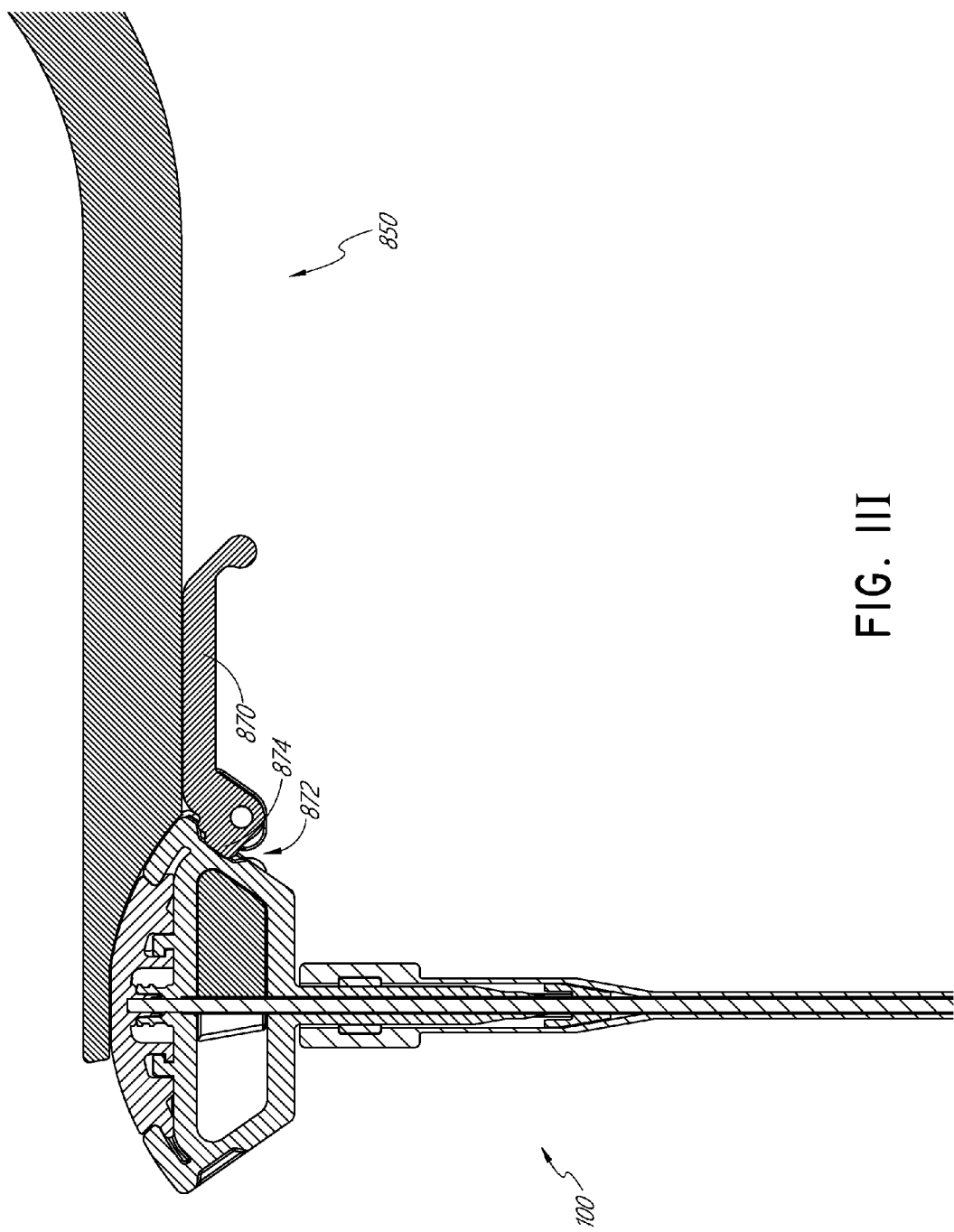

FIGS. 11F-11I illustrate an embodiment of an impact handle 850 including a locking cam in further detail. In this embodiment, the vertical position of the locking cam 870, shown in FIGS. 11F and 11G, is the unlocked position, and the horizontal position, shown in FIGS. 11H-11I, is the locked position. As shown in FIG. 11F, the first end 870a of the locking cam 870 that is pivotally coupled to the body portion 853 of the attachment portion 852 includes a protrusion or tab 874. The side 124a of the cannula handle 124 includes a slot 872 configured to receive the tab 874. When the locking cam 870 is rotated from the horizontal position to the vertical position, as shown in FIG. 11H, the tab 874 slides into engagement with the slot 872, as shown in the section view of FIG. 11I. The engagement of the tab 874 with the slot 872 provides frictional resistance to help hold the impact handle 850 securely in place and helps prevent or inhibit torsional movement between the impact handle 850 and needle assembly 100.

In the embodiments of FIGS. 11A-11E, the body portion 803 extends over and contacts a proximal side portion 124b of the cannula handle 124 and a portion of the top of the stylet handle 114. The impact strikeplate 806 extends from a distal end of the body portion 803 contacting the stylet handle 114 proximally along a portion of the impact handle 800. In some embodiments, a length of the impact strikeplate 806, indicated by l in FIG. 11E, can be about 2 inches to about 6 inches. For example, in one embodiment, the length l can be about 4 inches. In other embodiments, the length l can be less than 2 inches or more than 6 inches. Because the impact strikeplate 806 extends over the top of the needle assembly, the user can achieve substantially the same effect as using a mallet directly on the needle assembly handle while protecting the needle assembly from impact forces and being able to hold the handle portion 804 out of the way of any imaging or other equipment and away from potentially damaging radiation exposure. Alternatively, the user can use the mallet on a more proximal portion of the impact strikeplate 806 offset from the top of the needle assembly. In some embodiments, the impact handle 800 can include a secondary impact strikeplate 806b at a proximal end of the handle portion 804. The user can choose to use a mallet or similar instrument on either or both of the impact strikeplate 806 and secondary impact strikeplate 806b. The strikeplate 856 of the embodiment of FIGS. 11F-11I also extends over the top of the needle assembly 100, but is longer than the strikeplate 806 of the impact handle 800 of FIGS. 11A-11E. A longer strikeplate 856 can advantageously provide a greater surface area for the surgeon to use the mallet.

In some embodiments, an impact handle can be a folding handle, for example as shown in FIG. 12. In the illustrated embodiment, the impact handle 900 includes a first portion 900a coupled to a second portion 900b by a pivot 908. The first portion 900a includes the handle portion 904, and the second portion 900b includes the attachment portion 902. The folding arrangement can advantageously allow the handle to be placed in a smaller and more easily handled package for shipping and storage. In some embodiments, the folding handle 900 can also allow the first portion 900a to be rotated to various angles relative to the second portion 900b. For example, the handle 900 can include stop points at 90°, 120°, and or any other angular position. This adjustability can advantageously allow the user to select different angles to help with positioning and holding the handle 900.

Any of the attachment mechanisms shown and described herein can be used with any of the impact handle configurations shown and described herein. For example, an impact handle can have a curved shape similar to that of impact handle 300 as shown in FIGS. 3A-3B with the attachment mechanism similar to that of attachment portion 602 shown in FIGS. 7A-7E, attachment portion 702 shown in FIGS. 9A-9B, attachment portion 752 shown in FIGS. 10A-10B or any other suitable attachment portion. An angled or straight impact handle can also have any of the attachment mechanisms shown and described herein. Other impact handle configurations and attachment mechanisms are also possible. For example, the attachment portion can couple to the needle assembly via threading, twisting, snapping, clipping, or other means. Additionally, although an impact handle according to the present disclosure can include an impact strikeplate at a proximal end of the handle portion, on a top surface of a body portion of the impact handle configured to be adjacent the needle assembly handle in use, or elsewhere on the impact handle, a user may still choose to use a mallet or similar instrument directly on the needle assembly itself if he or she wishes, or may choose not to use a mallet or similar instrument at all. In such cases, the impact handle can still allow the user to hold the needle assembly while keeping his or her hand(s) out of or farther away from the radiation and/or to maneuver the needle assembly to the desired position and hold the needle assembly in the desired position more easily. Furthermore, an impact handle according to the present disclosure need not include an impact strikeplate at all.

Additionally, some impact handle embodiments can be configured to couple to specific needle assemblies. Other impact handle embodiments can be universal and can be configured to couple to a variety of needle assembly variations. For example, impact handles 200, 300, 400, 450, 500, 800, and 850 can have attachment portions configured to specifically couple to a needle assembly having a shape and configuration as shown herein. Impact handles 600, 700, and 750 can be configured to couple to a variety of needle assemblies. Attachment portions such as those on impact handles 200, 300, 400, 450, 500, and 800 can also be modified for use with needle assemblies having shapes and/or configurations different than those shown herein.

Figure 13A:
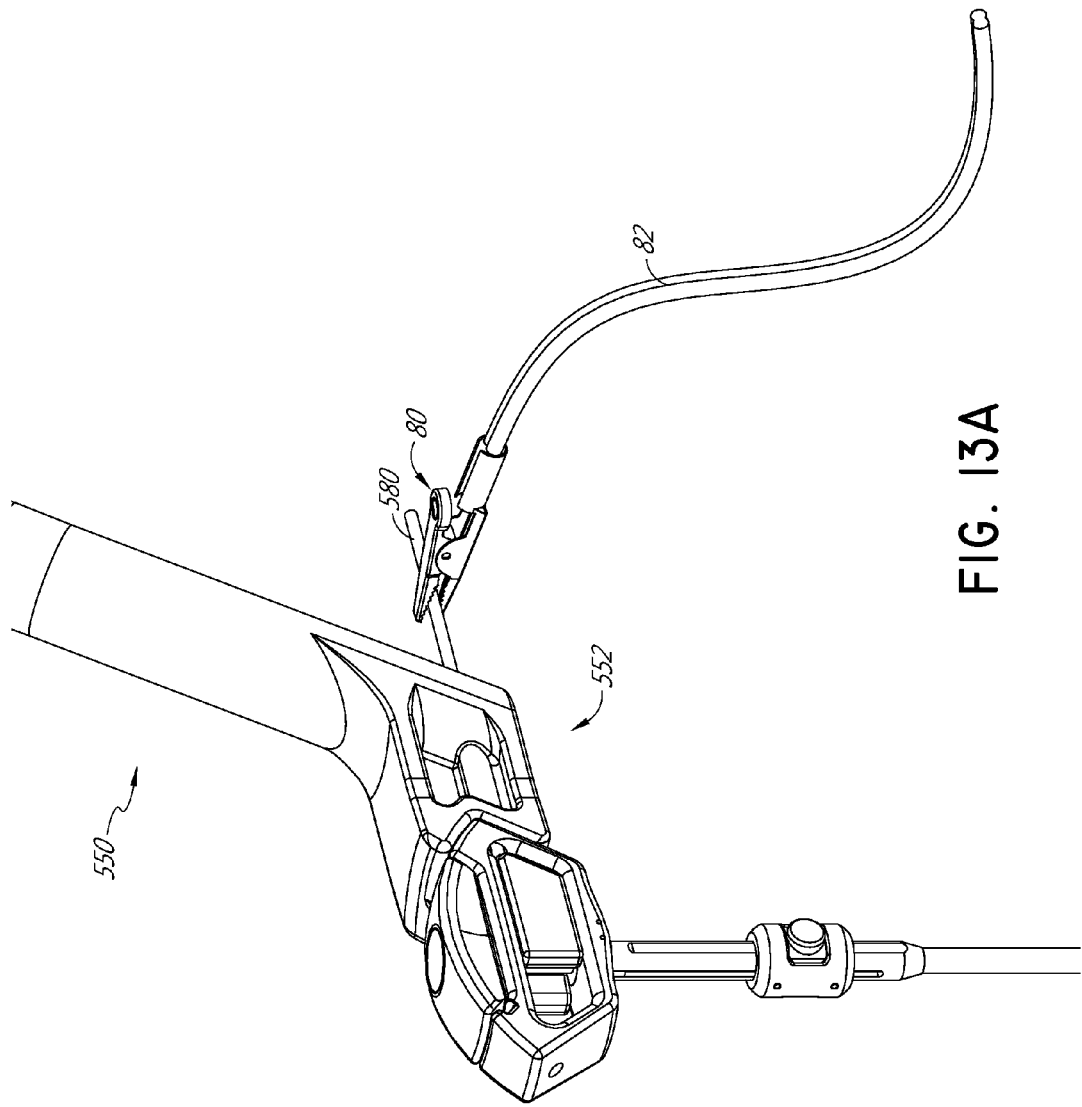
FIG. 13A illustrates a partial front perspective view of another embodiment of an impact handle coupled to a Jamshidi needle.
Figure 13B:
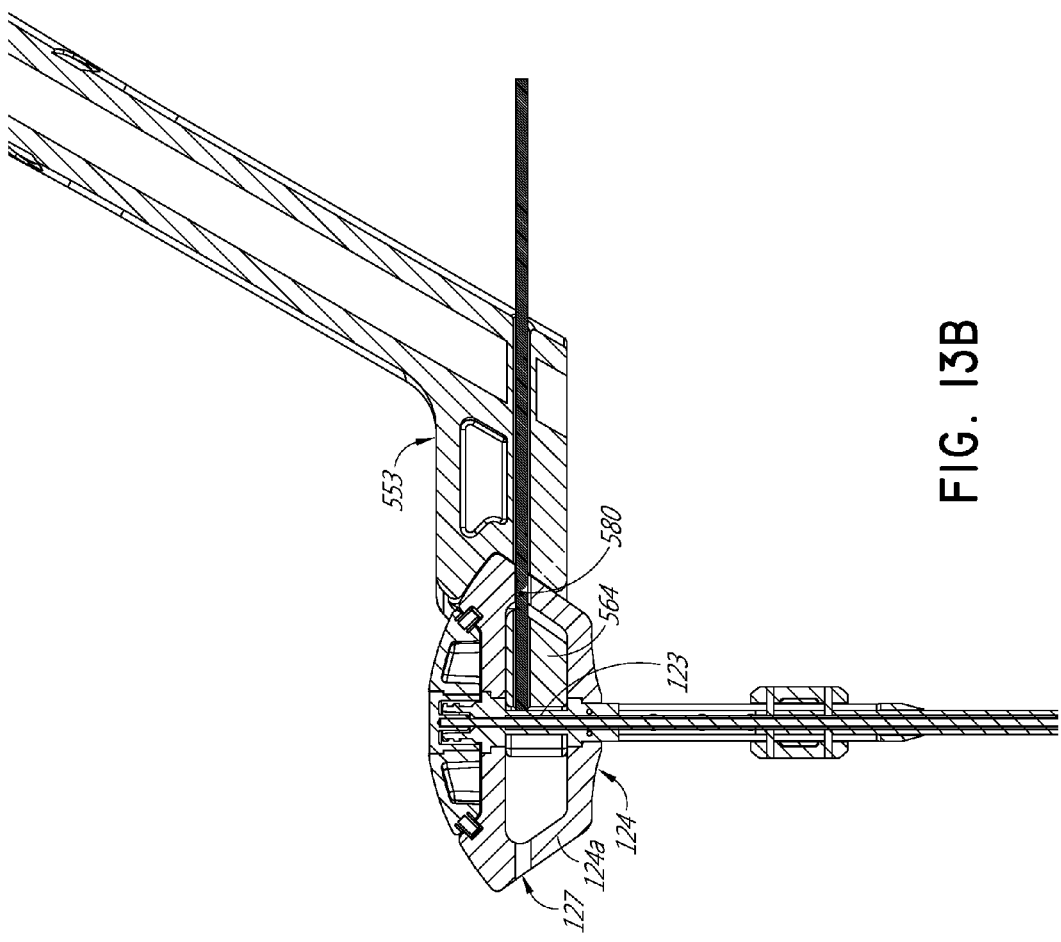
FIG. 13B illustrates a partial front section view of the impact handle coupled to the Jamshidi needle of FIG. 13A.

In some embodiments, an impact handle according to the present disclosure can be configured for use with a needle assembly configured for neuromonitoring. For example, in some embodiments, an impact handle can include a conductive pin extending through at least a portion of the impact handle, for example, as shown in FIGS. 13A and 13B. In the illustrated embodiment, the conductive pin 580 extends through the body portion 553 and connector 564 of the attachment portion 552 of the impact handle 550. In some embodiments, the pin 580 is removably and/or slidably received through the attachment portion 552. As shown in FIG. 13B, one or both sides 124a of the cannula handle 124 can include an aperture 127 configured to receive the pin 580. In some embodiments, the impact handle 550 is coupled to the needle assembly 100, and then the pin 580 is slid through the body portion 553, aperture 127, and connector 564 to contact the post 123 of the needle assembly cannula shaft. In some embodiments, the pin 580 can extend through the post 123 portion of the cannula shaft 122 to contact the stylet shaft 112. The pin 580 can function as a connection point for a source of electrical stimulation. For example, as shown in FIG. 13A, an electrical conduit 82 can include a connector, such as an alligator clip 80. As shown, the user can couple the alligator clip 80 to the conductive pin 580. The conductive pin 580 can be made of or include a conductive material, for example, a metal, to conduct electrical current from the conduit 82 and alligator clip 80 to the post 123. The electrical stimulation can then travel along the length of the needle assembly (through the cannula shaft 122 and/or stylet shaft 112) and can allow for neuromonitoring during various procedures.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A kit comprising:
    a needle assembly comprising:
        a cannula shaft; and
        a cannula handle coupled to a proximal-most end of the cannula shaft, wherein a width of the cannula handle extends beyond a width of the cannula shaft in a plane offset from a longitudinal axis of the cannula shaft and an impact handle comprising:
        an attachment portion configured to couple to the needle assembly;
        a handle portion extending from the attachment portion and configured to be gripped in use; and
        an impact strikeplate, the impact strikeplate configured to be struck with a mallet in use and configured to transfer forces from the mallet to the needle assembly to drive at least a portion of the needle assembly into bone, wherein the attachment portion and the impact strikeplate are a single piece;
        wherein the attachment portion comprises a connector, the connector configured to directly engage a portion of the cannula shaft below a proximal-most end of the cannula handle.

2. The kit of claim 1, wherein the handle portion extends from the attachment portion at an angle.

3. The kit of claim 1, wherein the impact strikeplate is on a proximal end of the handle portion.

4. The kit of claim 1, wherein a top surface of the attachment portion comprises the impact strikeplate.

5. The kit of claim 4, wherein the top surface of the attachment portion extends over at least part of a handle portion of the needle assembly when the attachment portion is coupled to the needle assembly.

6. The kit of claim 1, wherein a longitudinal axis of the attachment portion extends at a non-parallel angle to a long axis of the cannula shaft when coupled to the needle assembly, the handle portion extends parallel to the long axis of the cannula shaft when the attachment portion is coupled to the needle assembly, and a curved portion extends between the attachment portion and handle portion.

7. The kit of claim 1, wherein the attachment portion further comprises a locking mechanism configured to secure the attachment portion to the needle assembly in a locked position.

8. The kit of claim 1, wherein the cannula shaft has a constant diameter.

9. The kit of claim 8, wherein the cannula handle includes a central opening and a portion of the cannula shaft extends across the central opening, and wherein the connector is configured to be disposed in the central opening when the attachment portion is coupled to the needle assembly, the connector comprising a notch configured to engage the portion of the cannula shaft extending across the central opening.

10. A kit comprising:
a needle assembly comprising:
 a cannula shaft; and
 a cannula handle coupled to a proximal end of the cannula shaft; and
an impact handle comprising:
 an attachment portion configured to couple to a portion of the cannula shaft;
 a handle portion extending from the attachment portion and configured to be gripped in use; and
 an impact strikeplate, the impact strikeplate configured to be struck with a mallet in use and configured to transfer forces from the mallet to the needle assembly,
wherein the cannula handle includes a central opening and a portion of the cannula shaft extends across the central opening, and wherein the attachment portion of the impact handle comprises a connector configured to be disposed in the central opening when the attachment portion is coupled to the needle assembly, the connector comprising a notch configured to engage the portion of the cannula shaft extending across the central opening,
wherein the attachment portion further comprises a recess configured to receive a side of the cannula handle when the attachment portion is coupled to the needle assembly, wherein the recess is partially bordered by the connector.

11. The kit of claim 10, wherein the side of the cannula handle comprises a slot, the attachment portion comprises a locking cam configured to secure the impact handle to the needle assembly in a locked position, and the locking cam comprises a tab configured to be received in the slot when the attachment portion is coupled to the needle assembly and the locking cam is in the locked position.

12. A kit comprising: a needle assembly comprising:
a stylet comprising a stylet shaft and a stylet handle coupled to a proximal-most end of the stylet shaft, the stylet shaft having a sharp distal tip, wherein a width of the stylet handle extends beyond a width of the stylet shaft in a plane offset from a longitudinal axis of the stylet shaft; and
a cannula comprising a cannula shaft and a cannula handle coupled to a proximal end of the cannula shaft, the cannula shaft having a lumen therethrough, wherein the stylet shaft is configured to be disposed in the lumen of the cannula shaft, wherein the stylet handle is configured to removably couple to the cannula handle; and
an extension handle configured to be coupled to the needle assembly and comprising:
an attachment portion configured to couple to the needle assembly; a handle portion extending from the attachment portion and configured to be gripped in use; and
an impact strikeplate, the impact strikeplate configured to be struck with a mallet in use and configured to transfer forces from the mallet to the needle assembly.

13. The kit of claim 12, wherein the cannula handle couples to a proximal-most end of the cannula shaft, wherein the attachment portion is configured to contact a portion of one or more of the cannula shaft and the cannula handle when the attachment portion is coupled to the needle assembly.

14. The kit of claim 13, wherein the cannula handle includes a central opening and a portion of the cannula shaft extends across the central opening, and wherein the attachment portion of the extension handle comprises a connector configured to be disposed in the central opening when the attachment portion is coupled to the needle assembly, the connector comprising a notch configured to engage the portion of the cannula shaft extending across the central opening.

15. The kit of claim 1, wherein when the attachment portion is coupled to the needle assembly, the attachment portion is configured to contact a portion of the cannula handle.

16. The kit of claim 1, wherein when the attachment portion is coupled to the needle assembly, the attachment portion and the impact strikeplate are configured to rotate about a longitudinal axis of the needle assembly.

17. The kit of claim 1, wherein the attachment portion comprises a locking cam configured to secure the impact handle to the needle assembly in a locked position, and the locking cam comprises a tab configured to be received in a slot of the needle assembly when the attachment portion is coupled to the needle assembly and the locking cam is in the locked position.

18. The kit of claim 12, wherein a top surface of the cannula handle is configured to receive the stylet handle when the attachment portion is coupled to the needle assembly.

19. The kit of claim 12, wherein when the attachment portion is coupled to the needle assembly, the attachment portion is configured to contact the stylet handle.

20. The kit of claim 12, wherein when the attachment portion is coupled to the needle assembly, the attachment portion is configured to contact a side portion of the cannula handle and a top portion of the stylet handle.

21. The kit of claim 12, wherein the cannula handle includes a central opening and a portion of the cannula shaft extends across the central opening, and wherein the attachment portion is configured to rotatably engage the portion of the cannula shaft that extends across the central opening, wherein rotation of the attachment portion relative to the cannula shaft causes the impact strikeplate to rotate about a longitudinal axis of the needle assembly.

22. The kit of claim 12, wherein the attachment portion comprises a recess configured to receive a side of the cannula handle when the attachment portion is coupled to the needle assembly.

23. The kit of claim 22, wherein the cannula handle includes a central opening defining an interior wall of the side of the cannula handle, wherein when the recess receives the side of the cannula handle, the attachment portion contacts the interior wall of the side of the cannula handle and an exterior wall of the side of the cannula handle.

24. The kit of claim 12, wherein the attachment portion comprises a locking cam configured to secure the impact handle to the needle assembly in a locked position, and the locking cam comprises a tab configured to be received in a slot of the needle assembly when the attachment portion is coupled to the needle assembly and the locking cam is in the locked position.

25. A kit comprising:
a needle assembly comprising:
   a cannula shaft; and
   a cannula handle coupled to a proximal end of the cannula shaft; and
an impact handle comprising:
   an attachment portion configured to couple to the needle assembly, wherein the attachment portion comprises:
      a recess configured to receive a side of the cannula handle when the attachment portion is coupled to the needle assembly;
      a body portion;
      a sidewall extending distally from the body portion; and
      a connector extending distally from the sidewall, wherein a distal surface of the body portion, the sidewall,
   and a proximal surface of the connector define the recess;
      a handle portion extending from the attachment portion and configured to be gripped in use; and
      an impact strikeplate, the impact strikeplate configured to be struck with a mallet in use and configured to transfer forces from the mallet to the needle assembly.

26. The kit of claim 25, wherein when the attachment portion is coupled to the needle assembly, the attachment portion and the impact strikeplate are configured to rotate about a longitudinal axis of the needle assembly.

27. The kit of claim 25, wherein the connector further comprises a distal-facing notch configured to receive a portion of the needle assembly when the attachment portion is coupled to the needle assembly.

28. The kit of claim 25, wherein the attachment portion further comprises a locking mechanism configured to secure the attachment portion to the needle assembly in a locked position.

29. The kit of claim 25, wherein the attachment portion is configured to contact a portion of the cannula shaft when the attachment portion is coupled to the needle assembly.

30. A kit comprising:
a needle assembly comprising:
   a stylet comprising a stylet shaft and a stylet handle coupled to a proximal-most end of the stylet shaft, the stylet shaft having a sharp distal tip; and
   a cannula comprising a cannula shaft and a cannula handle coupled to a proximal end of the cannula shaft, the cannula shaft having a lumen therethrough, wherein a width of the cannula handle extends beyond a width of the cannula shaft in a plane offset from a longitudinal axis of the cannula shaft, wherein the stylet shaft is configured to be disposed in the lumen of the cannula shaft, wherein the stylet handle is configured to removably couple to the cannula handle; and
an extension handle configured to be coupled to the needle assembly and comprising:
   an attachment portion configured to couple to the needle assembly;
   a handle portion extending from the attachment portion and configured to be gripped in use; and
   an impact strikeplate, the impact strikeplate configured to be struck with a mallet in use and configured to transfer forces from the mallet to the needle assembly.

* * * * *